US012605553B1

(12) United States Patent  
Iamberger et al.

(10) Patent No.: US 12,605,553 B1  
(45) Date of Patent: Apr. 21, 2026

(54) IN SITU ASSEMBLY OF PROSTHETIC PACING VALVES

(71) Applicant: SMARTVALES LTD., Savyon (IL)

(72) Inventors: Meni Iamberger, Kfar Saba (IL); Navot Rabban, Ramat Gan (IL); Boaz Harari, Ganey Tikva (IL)

(73) Assignee: SMARTVALVES LTD, Savyon (IL)

( * ) Notice: Subject to any disclaimer, the term of this patent is extended or adjusted under 35 U.S.C. 154(b) by 0 days.

(21) Appl. No.: 19/068,620

(22) Filed: Mar. 3, 2025

Related U.S. Application Data

(60) Provisional application No. 63/760,353, filed on Feb. 19, 2025.

(51) Int. Cl.
| | |
|---|---|
| *A61N 1/362* | (2006.01) |
| *A61F 2/00* | (2006.01) |
| *A61F 2/24* | (2006.01) |
| *A61N 1/372* | (2006.01) |
| *A61N 1/375* | (2006.01) |
| *A61N 1/378* | (2006.01) |

(52) U.S. Cl.  
CPC ............ *A61N 1/362* (2013.01); *A61F 2/0095* (2013.01); *A61F 2/2409* (2013.01); *A61F 2/2418* (2013.01); *A61F 2/2427* (2013.01); *A61N 1/37229* (2013.01); *A61N 1/3758* (2013.01); *A61N 1/3787* (2013.01); *A61F 2210/0014* (2013.01); *A61F 2220/0008* (2013.01); *A61F 2230/0004* (2013.01); *A61F 2230/0069* (2013.01); *A61F 2250/006* (2013.01)

(58) Field of Classification Search  
CPC .................. A61F 2/2427–2429; A61F 2/2418  
See application file for complete search history.

(56) References Cited

U.S. PATENT DOCUMENTS

| | | |
|---|---|---|
| 3,745,995 A | 7/1973 | Kraus |
| 4,256,094 A | 3/1981 | Kapp et al. |
| | (Continued) | |

FOREIGN PATENT DOCUMENTS

| | | |
|---|---|---|
| CN | 110534284 B | 5/2022 |
| EP | 3 508 113 A1 | 7/2019 |
| | (Continued) | |

OTHER PUBLICATIONS

Zhongyu Dai, et al., "Selective Omnidirectional Magnetic Resonant Coupling Wireless Power Transfer With Multiple-Receiver System", IEEE Access, Feb. 2018, vol. 6, pp. 19287-19294.

(Continued)

*Primary Examiner* — Eric D. Bertram  
(74) *Attorney, Agent, or Firm* — Sughrue Mion, PLLC

(57) ABSTRACT

An electrical-component add-on is provided for use with a prosthetic cardiac valve including a tubular frame. The electrical-component add-on includes a support and one or more electrical components. The support is (a) configured to assume delivery and deployed configurations, (b) configured to be positioned above, at, or below an annulus of a native cardiac valve of a heart, and (c) shaped as a ring when in the deployed configuration, so as to receive the tubular frame of the prosthetic cardiac valve within the support. The one or more electrical components are supported by the support, and include an antenna and one or more electrodes. Other embodiments are also described.

24 Claims, 21 Drawing Sheets

(56) References Cited

U.S. PATENT DOCUMENTS

| | | | |
|---|---|---|---|
| 4,458,695 A | | 7/1984 | Peers-Trevarton |
| 4,979,955 A | | 12/1990 | Smith |
| 5,487,760 A | * | 1/1996 | Villafana ............... A61F 2/2403 |
| | | | 607/33 |
| 6,030,335 A | | 2/2000 | Franchi |
| 6,030,336 A | | 2/2000 | Franchi |
| 6,050,932 A | | 4/2000 | Franchi |
| 6,473,653 B1 | | 10/2002 | Schallhorn et al. |
| 7,643,879 B2 | | 1/2010 | Shuros et al. |
| 7,914,569 B2 | | 3/2011 | Nguyen et al. |
| 8,036,743 B2 | | 10/2011 | Savage et al. |
| 8,092,365 B2 | | 1/2012 | Rinderknecht et al. |
| 8,239,023 B2 | | 8/2012 | Shuros et al. |
| 8,471,562 B2 | | 6/2013 | Knizhnik |
| 8,591,567 B2 | * | 11/2013 | Chau ..................... A61F 2/243 |
| | | | 604/103.08 |
| 8,628,525 B2 | | 1/2014 | Wirtz et al. |
| 8,704,721 B2 | | 4/2014 | Ferrer Herrera et al. |
| 9,005,106 B2 | | 4/2015 | Gross et al. |
| 9,314,334 B2 | * | 4/2016 | Chau ..................... A61F 2/2418 |
| 9,326,854 B2 | | 5/2016 | Casley et al. |
| 9,526,637 B2 | | 12/2016 | Dagan et al. |
| 9,662,211 B2 | | 5/2017 | Hodson et al. |
| 9,737,264 B2 | | 8/2017 | Braido et al. |
| 9,750,942 B2 | | 9/2017 | Saha et al. |
| 9,808,201 B2 | | 11/2017 | Braido et al. |
| 9,821,159 B2 | | 11/2017 | Ackermann et al. |
| 9,877,831 B2 | * | 1/2018 | Chau ..................... A61F 2/2433 |
| 10,543,083 B2 | | 1/2020 | Gross |
| 10,667,906 B2 | * | 6/2020 | Chau ..................... A61F 2/2418 |
| 10,758,725 B2 | | 9/2020 | Daniels et al. |
| 10,835,750 B2 | | 11/2020 | Gross |
| 11,013,597 B2 | | 5/2021 | Gross |
| 11,065,451 B1 | | 7/2021 | Gross |
| 11,096,605 B2 | | 8/2021 | Wald et al. |
| 11,931,255 B1 | | 3/2024 | Gross et al. |
| 11,975,203 B1 | | 5/2024 | Gross et al. |
| 2003/0032853 A1 | | 2/2003 | Korakianitis et al. |
| 2004/0024285 A1 | | 2/2004 | Muckter |
| 2004/0097784 A1 | | 5/2004 | Peters et al. |
| 2004/0111006 A1 | | 6/2004 | Alferness et al. |
| 2005/0049696 A1 | | 3/2005 | Siess et al. |
| 2006/0178707 A1 | | 8/2006 | Thomas et al. |
| 2006/0206170 A1 | | 9/2006 | Denker et al. |
| 2006/0213682 A1 | | 9/2006 | Moon et al. |
| 2008/0077016 A1 | | 3/2008 | Sparks et al. |
| 2008/0215144 A1 | * | 9/2008 | Ryan ..................... A61F 2/2418 |
| | | | 623/2.18 |
| 2008/0269813 A1 | | 10/2008 | Greenhut et al. |
| 2010/0131039 A1 | * | 5/2010 | Chau ..................... A61F 2/2418 |
| | | | 623/1.12 |
| 2010/0197994 A1 | | 8/2010 | Mehmanesh |
| 2011/0071351 A1 | | 3/2011 | Sperling |
| 2011/0137370 A1 | | 6/2011 | Gross et al. |
| 2011/0196482 A1 | | 8/2011 | Forsell |
| 2012/0197350 A1 | | 8/2012 | Roberts et al. |
| 2012/0245678 A1 | | 9/2012 | Solem |
| 2012/0265296 A1 | | 10/2012 | McNamara et al. |
| 2012/0296382 A1 | | 11/2012 | Shuros et al. |
| 2013/0138205 A1 | | 5/2013 | Kushwaha et al. |
| 2013/0297009 A1 | | 11/2013 | Chalekian et al. |
| 2014/0066895 A1 | | 3/2014 | Kipperman |
| 2014/0081154 A1 | | 3/2014 | Toth |
| 2014/0081389 A1 | * | 3/2014 | Chau ..................... A61F 2/243 |
| | | | 623/2.11 |
| 2014/0180391 A1 | | 6/2014 | Dagan et al. |
| 2014/0275720 A1 | | 9/2014 | Ferrari |
| 2015/0128684 A1 | | 5/2015 | Hudson et al. |
| 2016/0045165 A1 | | 2/2016 | Braido et al. |
| 2016/0045316 A1 | | 2/2016 | Braido et al. |
| 2016/0144091 A1 | | 5/2016 | Breedon et al. |
| 2016/0220368 A1 | * | 8/2016 | Chau ..................... A61F 2/243 |
| 2016/0278951 A1 | | 9/2016 | Dagan et al. |
| 2017/0027689 A1 | * | 2/2017 | Marcelli ............... A61F 2/2403 |
| 2017/0100527 A1 | | 4/2017 | Schwammenthal et al. |
| 2017/0258585 A1 | * | 9/2017 | Marquez .............. A61B 5/4851 |
| 2017/0266433 A1 | | 9/2017 | Daniels et al. |
| 2018/0147060 A1 | * | 5/2018 | Chau ..................... A61F 2/2418 |
| 2019/0076588 A1 | | 3/2019 | Ochsner et al. |
| 2019/0209302 A1 | | 7/2019 | Gross |
| 2020/0139121 A1 | * | 5/2020 | Gross ................. A61N 1/37518 |
| 2020/0261224 A1 | * | 8/2020 | Gross ..................... A61N 1/371 |
| 2020/0282204 A1 | | 9/2020 | Capek et al. |
| 2020/0324033 A1 | | 10/2020 | Agah et al. |
| 2021/0283397 A1 | * | 9/2021 | Gross ..................... A61B 5/318 |
| 2022/0167922 A1 | | 6/2022 | Gross et al. |
| 2022/0287851 A1 | | 9/2022 | Goldberg et al. |
| 2023/0218180 A1 | | 7/2023 | Mujeeb-U-Rahman et al. |
| 2023/0329865 A1 | | 10/2023 | Kappetein et al. |
| 2024/0164642 A1 | | 5/2024 | Hunter et al. |
| 2024/0415640 A1 | | 12/2024 | Basude et al. |
| 2025/0058124 A1 | | 2/2025 | Gross et al. |

FOREIGN PATENT DOCUMENTS

| | | |
|---|---|---|
| EP | 3 785 758 A1 | 3/2021 |
| FR | 3034650 A1 | 10/2016 |
| WO | 2013/035092 A2 | 3/2013 |
| WO | 2013/111137 A2 | 8/2013 |
| WO | 2014/043235 A1 | 3/2014 |
| WO | 2015/200707 A1 | 12/2015 |
| WO | 2016/157183 A1 | 10/2016 |
| WO | 2018/142186 A1 | 8/2018 |
| WO | 2020/210490 A1 | 10/2020 |
| WO | 2020257759 A1 | 12/2020 |
| WO | 2021086707 A1 | 5/2021 |
| WO | 2021/140507 A1 | 7/2021 |
| WO | 2021/224904 A1 | 11/2021 |
| WO | 2022051716 A1 | 3/2022 |
| WO | 2022/149130 A1 | 7/2022 |
| WO | 2025/041129 A1 | 2/2025 |

OTHER PUBLICATIONS

Office Action dated Dec. 21, 2023 in U.S. Appl. No. 18/452,216.
Notice of Allowance dated Sep. 26, 2019, which issued during the prosecution of U.S. Appl. No. 15/864,661.
Notice of Allowance dated Nov. 15, 2023 in U.S. Appl. No. 18/452,229.
Notice of Allowance dated Jan. 25, 2021, which issued during the prosecution of U.S. Appl. No. 16/868,121.
Notice of Allowance dated Aug. 3, 2020, which issued during the prosecution of U.S. Appl. No. 16/734,798.
Michael Traskos, "Should Polymide Insulated Wire be Trusted?", Lectromec, Sep. 25, 2018, pp. 1-7.
Harwin, "Hi-Rel Flex Circuit Assemblies," Product Brochure, Jul. 11, 2022, CP054/07112022, pp. 1-13.
Gerald E. Loeb, et al. "BION System for distributed neural prosthetic interfaces", Medical Engineering & Physics, 2001, vol. 23, pp. 8-19 (10 pages).
European Search Report dated May 17, 2019 which issued during the prosecution of Applicant's European App No. 19150581.7.
Ding Han, et al., "A Three-Dimensional Orthogonal Receiving Coil for In Vivo Microrobot Wireless Power Transmission Systems", Energies, 2022, vol. 15, No. 6321, pp. 1-13.
An Office Action dated Nov. 23, 2020, which issued during the prosecution of U.S. Appl. No. 16/868,121.
An Office Action dated Apr. 27, 2020, which issued during the prosecution of U.S. Appl. No. 16/734,798.
An Office Action dated Apr. 11, 2019, which issued during the prosecution of U.S. Appl. No. 15/864,661.
An International Search Report (ISR) and Written Opinion issued in PCT/IL2022/050019, dated May 6, 2022.
Jobanputra Y et al., "Rapid Ventricular Pacing During Transcatheter Valve Procedures Using An Internal Device And Programmer: A Demonstration Of Feasibility," JACC Mar. 20, 2018, vol. 71, Issue 11, p. 1381.
An International Search Report (ISR) and Written Opinion issued in PCT/IL2021/050017, dated Jun. 9, 2021.

(56) References Cited

OTHER PUBLICATIONS

Ahran S Arnold, et al., "His-Purkinje Conduction System Pacing: State of the Art in 2020", Arrhythmia & Electrophysiology Review, 2020, vol. 9, No. 3, pp. 136-145 (10 pages).

A Notice of Allowance issued in U.S. Appl. No. 17/328,588 dated Mar. 10, 2022.

Notice of Allowance dated Mar. 22, 2021, which issued during the prosecution of U.S. Appl. No. 17/142,729.

A Corrected International Search Report (ISR) and Written Opinion issued in PCT/IL2021/050016, dated Sep. 20, 2021.

A Communication under Art 94(3) EPC issued in European Appl. No. EP19150581.7, dated Aug. 30, 2022.

"Pacing at the Bundle of His," Medtronic, Inc., Minneapolis, MN, USA (Oct. 2017).

Office Action dated Jan. 17, 2024 in U.S. Appl. No. 18/452,216.

"Medtronic Evolut™ PRO System brochure," Medtronic, Inc., Minneapolis, MN, USA (Mar. 2017).

"Medtronic Core Valve™ System Instructions for Use," Medtronic, Inc., Minneapolis, MN, USA (2014).

International Search Report (PCT/ISA/210) and Written Opinion (PCT/ISA/237) dated Jan. 23, 2025 issued by the International Searching Authority in International Application No. PCT/IL2024/050830.

* cited by examiner

FIG. 20A
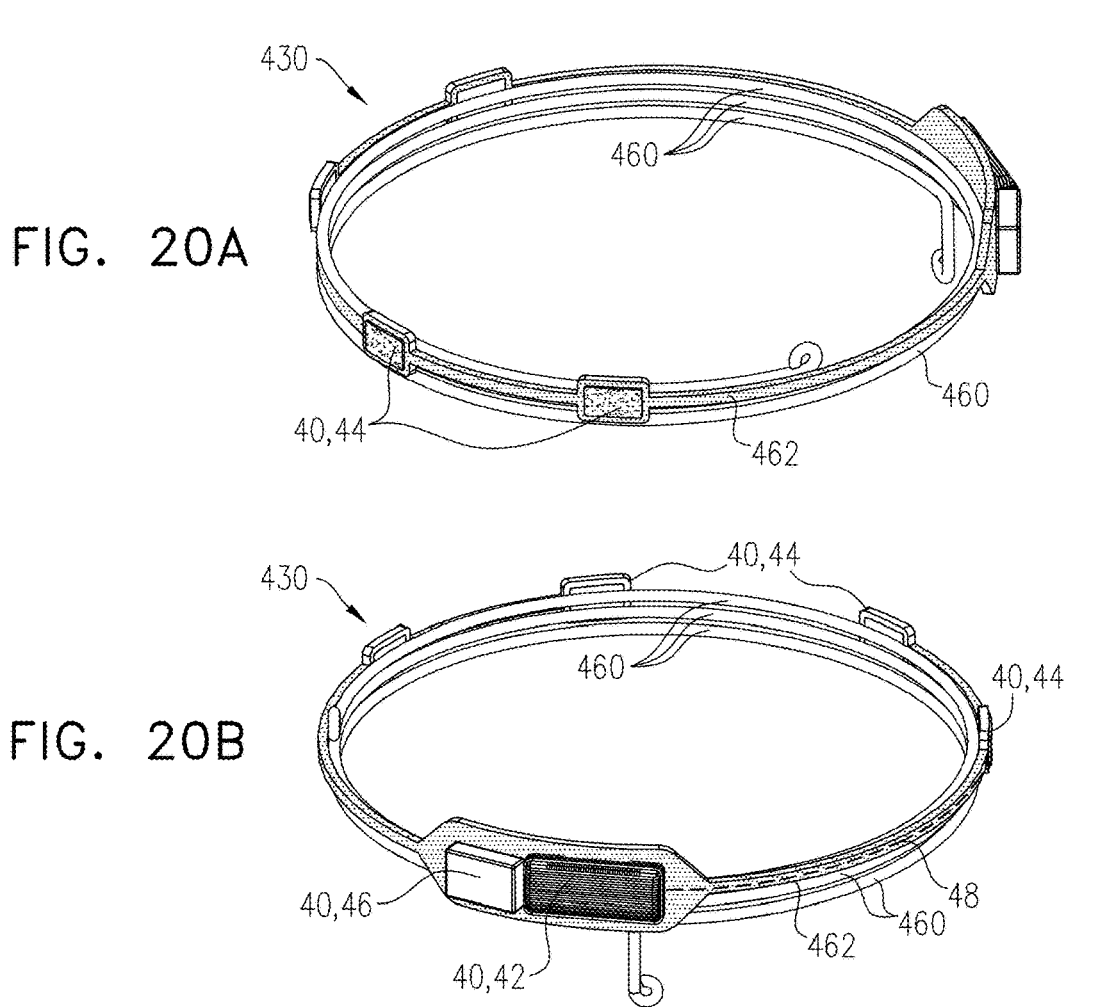
FIG. 20B
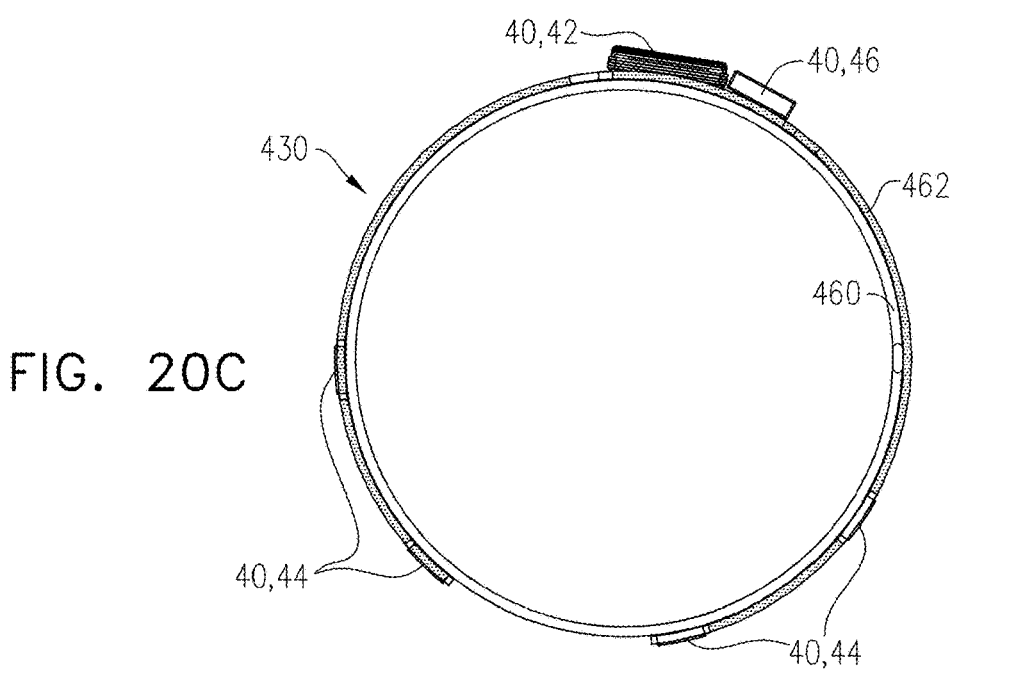
FIG. 20C

1

IN SITU ASSEMBLY OF PROSTHETIC PACING VALVES

CROSS-REFERENCE TO RELATED APPLICATIONS

The present application claims the benefit of U.S. Provisional Application 63/760,353, filed Feb. 19, 2025, which is assigned to the assignee of the present application and incorporated herein by reference.

The present application is related to:

U.S. application Ser. No. 19/068,707, filed Mar. 3, 2025, on even date herewith, which claims the benefit of U.S. Provisional Application 63/760,353, filed Feb. 19, 2025, and which is assigned to the assignee of the present application and incorporated herein by reference; and U.S. application Ser. No. 19/068,749, filed Mar. 3, 2025, on even date herewith, which claims the benefit of U.S. Provisional Application 63/760,353, filed Feb. 19, 2025, and which is assigned to the assignee of the present application and incorporated herein by reference.

FIELD OF THE APPLICATION

The present invention relates generally to surgical implants and systems, and specifically to prosthetic cardiac valve systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve replacement (TAVR). The most common complication is left bundle branch block (LBBB).

PCT Publication WO 2022/149130 to Gross, which is incorporated herein by reference, inter alia describes a prosthetic aortic valve, which is configured to be delivered to a native aortic valve of a patient in a constrained delivery configuration within a delivery sheath. The prosthetic aortic valve includes a frame, which includes interconnected stent struts arranged so as to define interconnected stent cells; a plurality of prosthetic leaflets coupled to the frame; a cathode and an anode, which are mechanically coupled to the frame; and a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath.

U.S. Pat. No. 11,975,203 to Gross et al. describes a prosthetic aortic valve that includes a frame including interconnected stent struts arranged so as to define interconnected stent cells. A plurality of prosthetic leaflets are coupled to the frame so as to allow blood flow in a downstream direction and inhibit blood flow in an upstream direction when the prosthetic aortic valve is in an expanded deployment configuration. Circuitry is mechanically coupled to the frame. An electrode is mechanically coupled to the frame. A printed circuit board (PCB) is shaped so as to define an elongate portion. An electrical lead electrically couples the electrode to the circuitry, and is integral with the elongate portion of the PCB. The elongate portion of the PCB is mechanically coupled to some of the interconnected stent struts of the frame. Other embodiments are also described.

WO 2022/046473 to Mujeeb-U-Rahman et al. describes a prosthetic valve that comprises a frame assembly having a first opening at an inflow portion of the frame assembly and a second opening at an outflow portion of the frame assembly, a first sensor device situated at the inflow portion of the frame, and a second sensor device situated at the outflow portion of the frame. Each of the first sensor device and the second sensor device is configured to sense a physical parameter and provide a sensor signal. The prosthetic valve further comprises a transmitter assembly configured to receive the sensor signals from the first sensor device and the second sensor device and wirelessly transmit a transmission signal based at least in part on the sensor signals.

SUMMARY OF THE APPLICATION

Some embodiments of the present invention provide electrical-component add-ons for attachment to a prosthetic cardiac valve. The electrical-component add-ons comprise a support and one or more electrical components, which are fixed to the support. Typically, the electrical components comprise an antenna and one or more electrodes. The electrical-component add-ons are typically configured to pace the heart and/or sense cardiac signals of the heart.

In some applications of the present invention, the electrical-component add-ons are configured to be easily attached to the prosthetic cardiac valve, such as by a healthcare worker. Typically, the healthcare worker attaches electrical-component add-on to the prosthetic cardiac valve during or soon before an implantation procedure in which the prosthetic cardiac valve and the attached electrical-component add-on are implanted in a body of a patient. For example, the electrical-component add-on may be attached to the prosthetic cardiac valve in an operating room or a cath lab.

In some of these applications, the support of the electrical-component add-on comprises a stretchable sheet, which is shaped so as to facilitate attachment of the support to a tubular frame of the prosthetic cardiac valve by stretching of the stretchable sheet. For some applications, the stretchable sheet is shaped so as to define one or more pockets, which are configured to facilitate the attachment of the support to the tubular frame.

In others of these applications, the tubular frame of the prosthetic cardiac valve defines respective snap-fastener first components. The support of the electrical-component add-on is shaped so as to define snap-fastener second components, which are configured to snappingly engage the snap-fastener first components, respectively, so as to attach the support to the tubular frame of the prosthetic cardiac valve.

In other applications of the present invention, the electrical-component add-ons are configured to be easily attached to the prosthetic cardiac valve within the patient's body by a surgeon during an implantation procedure. The support is configured to assume delivery and deployed configurations. The support is configured to be positioned above, at, or below an annulus of a native cardiac valve of a heart. The support is shaped as a ring when in the deployed configuration, so as to receive the tubular frame of the prosthetic cardiac valve within the support.

In some of these applications, the support of the electrical-component add-ons comprises a tubular stent comprising interconnected stent struts. In others of these applications, the support of the electrical-component add-ons comprises a wire having a shape memory that causes the wire to assume a ring shape when the support is in a deployed configuration.

There is therefore provided, in accordance with an application of the present invention, an electrical-component add-on for attachment to a prosthetic cardiac valve including a tubular frame defining interconnected stent struts arranged so as to define interconnected stent cells, the electrical-component add-on including:

a support, including a stretchable sheet, which is shaped so as to facilitate attachment of the support to the tubular frame of the prosthetic cardiac valve by stretching of the stretchable sheet; and one or more electrical components, which are fixed to the support, and which include an antenna and one or more electrodes.

For some applications, the one or more electrical components further include one or more electrical leads.

For some applications, the one or more electrical components further include circuitry.

For some applications, the circuitry is configured to pace a heart of a patient using at least one of the one or more electrodes.

For some applications, the one or more electrical components further include one or more electrical leads that electrically couple the one or more electrodes to the circuitry.

For some applications, the stretchable sheet has an elastic capacity of 20-60 cN/Tex.

For some applications, the stretchable sheet is elongatable, in at least one direction, by at least 10% of an initial length of the stretchable sheet, measured in the at least one direction while the stretchable sheet is unconstrained.

For some applications, the stretchable sheet, when unconstrained in a non-stretched state, has a surface area of 720-1000 mm2.

For some applications, the stretchable sheet, when unconstrained in a non-stretched state, has a greatest dimension of 45-65 mm.

For some applications, the stretchable sheet is shaped so as to facilitate the attachment of the support to the tubular frame without piercing of the stretchable sheet.

For some applications, the stretchable sheet is shaped so as to facilitate the attachment of the support to the tubular frame without stitching of the stretchable sheet.

For some applications, the stretchable sheet is configured such that when the support is attached to the tubular frame, the stretchable sheet surrounds less than 360 degrees of the tubular frame, with respect to a longitudinal axis of the tubular frame.

For some applications, the stretchable sheet is rotationally asymmetric when unconstrained.

For some applications, the electrical-component add-on further includes a sterile package, and the electrical-component add-on is sterile and is contained within the sterile package, which does not also contain the prosthetic cardiac valve.

For some applications, the stretchable sheet is shaped so as to define one or more pockets, which are configured to facilitate the attachment of the support to the tubular frame.

For some applications, the one or more pockets include a proximal pocket and a distal pocket, and the stretchable sheet is shaped so as to define the proximal pocket and the distal pocket.

For some applications, the one or more pockets include two or more distal pockets, and the stretchable sheet is shaped so as to define the proximal pocket and the two or more distal pockets.

For some applications, the one or more pockets include exactly one proximal pocket, and the stretchable sheet is shaped so as to define the exactly one proximal pocket and the two or more distal pockets.

For some applications:

the one or more pockets include a distal pocket, and the stretchable sheet is shaped so as to define the distal pocket, and one of the one or more electrodes is fixed to an external surface of the distal pocket.

For some applications:

the distal pocket is shaped to define a pocket opening on a first surface of the stretchable sheet, and the external surface of the distal pocket is defined by a second surface of the stretchable sheet opposite the first surface of the stretchable sheet.

For some applications:

the one or more pockets include a proximal pocket, and the stretchable sheet is shaped so as to define the proximal pocket, and the one or more electrical components further include circuitry, which is fixed to the proximal pocket.

For some applications, the stretchable sheet is shaped to facilitate the attachment of the support to one or more proximal stent cells at a proximal end of the tubular frame, and to one or more distal stent cells of the tubular frame at a distal end of the tubular frame.

For some applications, the stretchable sheet is shaped so as to define at least:

a proximal pocket, which is shaped to receive the one or more proximal stent cells, so as to facilitate the attachment of the support to the one or more proximal stent cells at the proximal end of the tubular frame, and a distal pocket, which is shaped to receive the one or more distal stent cells of the tubular frame, so as to facilitate the attachment of the support to the one or more distal stent cells at the distal end of the tubular frame.

For some applications, the stretchable sheet is shaped to facilitate the attachment of the support to two or more distal stent cells of the tubular frame at the distal end of the tubular frame.

For some applications, the stretchable sheet is shaped to facilitate the attachment of the support to three or more distal stent cells of the tubular frame at the distal end of the tubular frame.

For some applications, the stretchable sheet is shaped to facilitate the attachment of the support to no more than ten distal stent cells of the tubular frame at the distal end of the tubular frame.

For some applications:

the two or more distal stent cells include first and second distal stent cells, which are separated from each other around the tubular frame by at least one intervening third distal stent cell, and the stretchable sheet is shaped to facilitate the attachment of the support to the first and the second distal stent cells at the distal end of the tubular frame.

For some applications, the stretchable sheet is shaped to facilitate the attachment of the support to two or more proximal stent cells at the proximal end of the tubular frame.

For some applications, the two or more proximal stent cells are adjacent to each other around the tubular frame.

For some applications, the stretchable sheet is shaped so as to facilitate the attachment of the support to a radially-outward surface of the tubular frame.

For some applications, the stretchable sheet is shaped so as to facilitate the attachment of the support to the radially-outward surface of the tubular frame such that the stretchable sheet at least partially covers at least three stent cells.

For some applications, the stretchable sheet includes a stretchable fabric.

For some applications, a prosthetic cardiac valve system is provided that includes the electrical-component add-on and further includes the prosthetic cardiac valve.

For some applications:

the stent cells include distal stent cells at a distal end of the tubular frame, and the stretchable sheet is shaped to facilitate the attachment of the support to two or more of the distal stent cells of the tubular frame.

For some applications, the stretchable sheet is shaped to facilitate the attachment of the support to no more than 50% of the distal stent cells of the tubular frame.

For some applications, the prosthetic cardiac valve includes a plurality of prosthetic leaflets coupled to the tubular frame so as to allow blood flow in a proximal downstream direction and inhibit blood flow in a distal upstream direction.

For some applications:

the tubular frame is radially compressible, and is configured to elongate when radially compressed, and the stretchable sheet is configured to accommodate elongation of the tubular frame during radial compression and the elongation of the tubular frame while the support is attached to the tubular frame.

For some applications, the prosthetic cardiac valve system further includes first and second sterile packages, the electrical-component add-on is sterile and is contained within the first sterile package, and the prosthetic cardiac valve is sterile and is contained within the second sterile package.

There is further provided, in accordance with an application of the present invention, a method including:

bringing a support of an electrical-component add-on into contact with a tubular frame of a prosthetic cardiac valve, the support including a stretchable sheet, and the electrical-component add-on further including one or more electrical components, which are fixed to the support, and which include an antenna and one or more electrodes; and attaching the support to the tubular frame of the prosthetic cardiac valve by stretching the stretchable sheet.

For some applications, the method further includes, after attaching the support to the tubular frame, implanting the prosthetic cardiac valve and the electrical-component add-on in a body of a patient.

For some applications, the method further includes, after implanting the prosthetic cardiac valve and the electrical-component add-on, wirelessly transmitting energy to the antenna.

For some applications, the one or more electrical components further include one or more electrical leads.

For some applications, the one or more electrical components further include circuitry.

For some applications, the method further includes:

after attaching the support to the tubular frame, implanting the prosthetic cardiac valve and the electrical-component add-on in a body of a patient; and thereafter, wirelessly transmitting energy to the antenna and activating the circuitry to pace to a heart of a patient using at least one of the one or more electrodes.

For some applications, the one or more electrical components further include one or more electrical leads that electrically couple the one or more electrodes to the circuitry.

For some applications, attaching the support to the tubular frame includes elongating the stretchable sheet, in at least one direction, by at least 10% of an initial length of the stretchable sheet, measured in the at least one direction while the stretchable sheet is unconstrained.

For some applications, attaching the support to the tubular frame includes attaching the support to the tubular frame without piercing of the stretchable sheet.

For some applications, attaching the support to the tubular frame includes attaching the support to the tubular frame without stitching of the stretchable sheet.

For some applications, attaching the support to the tubular frame includes attaching the support to the tubular frame such that the stretchable sheet surrounds less than 360 degrees of the tubular frame, with respect to a longitudinal axis of the tubular frame.

For some applications, the stretchable sheet is rotationally asymmetric when unconstrained.

For some applications, the stretchable sheet is shaped so as to define one or more pockets, and attaching the support to the tubular frame includes using the one or more pockets to attach the support to the tubular frame.

For some applications, the one or more pockets include a proximal pocket and a distal pocket, and the stretchable sheet is shaped so as to define the proximal pocket and the distal pocket.

For some applications, the one or more pockets include two or more distal pockets, and the stretchable sheet is shaped so as to define the proximal pocket and the two or more distal pockets.

For some applications, the one or more pockets include exactly one proximal pocket, and the stretchable sheet is shaped so as to define the exactly one proximal pocket and the two or more distal pockets.

For some applications:

the one or more pockets include a distal pocket, and the stretchable sheet is shaped so as to define the distal pocket, and one of the one or more electrodes is fixed to an external surface of the distal pocket.

For some applications:

the distal pocket is shaped to define a pocket opening on a first surface of the stretchable sheet, and the external surface of the distal pocket is defined by a second surface of the stretchable sheet opposite the first surface of the stretchable sheet.

For some applications:

the one or more pockets include a proximal pocket, and the stretchable sheet is shaped so as to define the proximal pocket, and the one or more electrical components further include circuitry, which is fixed to the proximal pocket.

For some applications:

the tubular frame of the prosthetic cardiac defines interconnected stent struts arranged so as to define interconnected stent cells, and attaching the support to the tubular frame includes using the stretchable sheet to attach the support to one or more proximal stent cells at a proximal end of the tubular frame, and to one or more distal stent cells of the tubular frame at a distal end of the tubular frame.

For some applications:

the stretchable sheet is shaped so as to define at least a proximal pocket and a distal pocket, and attaching the support to the tubular frame includes:

using the proximal pocket to receive the one or more proximal stent cells, so as to attach the support to the one or more proximal stent cells at the proximal end of the tubular frame; and using the distal pocket to receive the one or more distal stent cells of the tubular frame, so as to attach the support to the one or more distal stent cells at the distal end of the tubular frame.

For some applications, attaching the support to the tubular frame includes using the stretchable sheet to attach the support to two or more distal stent cells of the tubular frame at the distal end of the tubular frame.

For some applications, attaching the support to the tubular frame includes using the stretchable sheet to attach the support to three or more distal stent cells of the tubular frame at the distal end of the tubular frame.

For some applications, attaching the support to the tubular frame includes using the stretchable sheet to attach the support to no more than ten distal stent cells of the tubular frame at the distal end of the tubular frame.

For some applications, attaching the support to the tubular frame includes using the stretchable sheet to attach the support to no more than 50% of the distal stent cells of the tubular frame.

For some applications:

the two or more distal stent cells include first and second distal stent cells, which are separated from each other around the tubular frame by at least one intervening third distal stent cell, and attaching the support to the tubular frame includes using the stretchable sheet to attach the support to the first and the second distal stent cells at the distal end of the tubular frame.

For some applications, attaching the support to the tubular frame includes using the stretchable sheet to attach the support to two or more proximal stent cells at the proximal end of the tubular frame.

For some applications, the two or more proximal stent cells are adjacent to each other around the tubular frame.

For some applications, attaching the support to the tubular frame includes using the stretchable sheet to attach the support to a radially-outward surface of the tubular frame.

For some applications:

the tubular frame of the prosthetic cardiac defines interconnected stent struts arranged so as to define interconnected stent cells, and using the stretchable sheet to attach the support to a radially-outward surface of the tubular frame includes using the stretchable sheet to attach the support to a radially-outward surface of the tubular frame such that the stretchable sheet at least partially covers at least five stent cells.

For some applications, the stretchable sheet includes a stretchable fabric.

For some applications, the prosthetic cardiac valve includes a plurality of prosthetic leaflets coupled to the tubular frame so as to allow blood flow in a proximal downstream direction and inhibit blood flow in a distal upstream direction.

For some applications, the method further includes, after attaching the support to the tubular frame, radially compressing the tubular frame such that the tubular frame elongates, and the stretchable sheet is configured to accommodate elongation of the tubular frame during the radial compression and the elongation of the tubular frame while the support is attached to the tubular frame.

For some applications:

the method further includes, after attaching the support to the tubular frame:

radially compressing the tubular frame; and thereafter, implanting the prosthetic cardiac valve and the electrical-component add-on in a body of a patient, and the method does not include inserting the radially-compressed tubular frame and the support into a sterile package after radially compressing the tubular frame.

For some applications:

the method further includes, after attaching the support to the tubular frame, radially compressing the tubular frame, and the method does not include inserting the radially-compressed tubular frame and the support into a sterile package after attaching the support to the tubular frame.

For some applications:

the electrical-component add-on is sterile and is contained within a first sterile package, the prosthetic cardiac valve is sterile and is contained within a second sterile package, and the method further includes, before bringing the support of the electrical-component add-on into contact with the tubular frame of the prosthetic cardiac valve:

removing the electrical-component add-on from the first sterile package; and removing the prosthetic cardiac valve from the second sterile package.

There is still further provided, in accordance with an application of the present invention, an electrical-component add-on for attachment to a prosthetic cardiac valve including a tubular frame defining respective snap-fastener first components and defining interconnected stent struts arranged so as to define interconnected stent cells, the electrical-component add-on including:

a support, which is shaped so as to define snap-fastener second components, which are configured to snappingly engage the snap-fastener first components, respectively, so as to attach the support to the tubular frame of the prosthetic cardiac valve; and one or more electrical components, which are fixed to the support, and which include an antenna and one or more electrodes.

For some applications, the snap-fastener second components are shaped so as to define respective studs.

For some applications, the snap-fastener second components are shaped so as to define respective sockets.

For some applications, the support includes support struts, which are shaped so as to define the snap-fastener second components.

For some applications:

the one or more electrical components further include one or more electrical leads, the support struts include electrical insulation, and a portion of the support struts electrically insulates the one or more electrical leads.

For some applications, the one or more electrical components further include one or more electrical leads.

For some applications, the one or more electrical components further include circuitry.

For some applications, the circuitry is configured to pace a heart of a patient using at least one of the one or more electrodes.

For some applications, the one or more electrical components further include one or more electrical leads that electrically couple the one or more electrodes to the circuitry.

For some applications, the support is elongatable, in at least one direction, by at least 2% of an initial length of the support, measured in the at least one direction while the support is unconstrained.

For some applications, the support, when unconstrained, has a greatest dimension of 45-65 mm.

For some applications, the support is configured such that when the support is attached to the tubular frame, the support surrounds less than 360 degrees of the tubular frame, with respect to a longitudinal axis of the tubular frame.

For some applications, the support is rotationally asymmetric when unconstrained.

For some applications, the electrical-component add-on further includes a sterile package, and the electrical-component add-on is sterile and is contained within the sterile package, which does not also contain the prosthetic cardiac valve.

For some applications, the snap-fastener second components are located on the support so as to facilitate attachment of the support to one or more proximal stent cells at a proximal end of the tubular frame, and to one or more distal stent cells of the tubular frame at a distal end of the tubular frame.

For some applications, the snap-fastener second components are located on the support so as to facilitate the attachment of the support to two or more distal stent cells of the tubular frame at the distal end of the tubular frame.

For some applications, the snap-fastener second components are located on the support so as to facilitate the attachment of the support to three or more distal stent cells of the tubular frame at the distal end of the tubular frame.

For some applications, the snap-fastener second components are located on the support so as to facilitate the attachment of the support to no more than ten distal stent cells of the tubular frame at the distal end of the tubular frame.

For some applications:
the two or more distal stent cells include first and second distal stent cells, which are separated from each other around the tubular frame by at least one intervening third distal stent cell, and
the snap-fastener second components are located on the support so as to facilitate the attachment of the support to the first and the second distal stent cells at the distal end of the tubular frame.

For some applications, the snap-fastener second components are located on the support so as to facilitate the attachment of the support to two or more proximal stent cells at the proximal end of the tubular frame.

For some applications, the two or more proximal stent cells are adjacent to each other around the tubular frame.

For some applications, the support is shaped so as to facilitate attachment of the support to a radially-outward surface of the tubular frame.

For some applications, a prosthetic cardiac valve system is provided that includes the electrical-component add-on and further includes the prosthetic cardiac valve.

For some applications:
the snap-fastener second components are shaped so as to define respective studs, and the snap-fastener first components are shaped as to define sockets for receiving the studs, respectively.

For some applications:
the snap-fastener first components are shaped so as to define respective studs, and
the snap-fastener second components are shaped as to define sockets for receiving the studs, respectively.

For some applications:
the support includes support struts, which are shaped so as to define the snap-fastener second components, and
the support struts and the stent struts are shaped such that the support struts generally run along a portion of the stent struts when the support is attached to the tubular frame.

For some applications:
the stent cells include distal stent cells at a distal end of the tubular frame, and
the snap-fastener second components are located on the support so as to facilitate attachment of the support to two or more of the distal stent cells of the tubular frame.

For some applications, the snap-fastener second components are located on the support so as to facilitate the attachment of the support to no more than 50% of the distal stent cells of the tubular frame.

For some applications, the prosthetic cardiac valve includes a plurality of prosthetic leaflets coupled to the tubular frame so as to allow blood flow in a proximal downstream direction and inhibit blood flow in a distal upstream direction.

For some applications:
the tubular frame is radially compressible, and is configured to elongate when radially compressed,
the support includes support struts, which are shaped so as to define the snap-fastener second components, and
the support struts are configured to accommodate elongation of the tubular frame during radial compression and the elongation of the tubular frame while the support is attached to the tubular frame.

For some applications, the prosthetic cardiac valve system includes first and second sterile packages,
the electrical-component add-on is sterile and is contained within the first sterile package, and
the prosthetic cardiac valve is sterile and is contained within the second sterile package.

There is additionally provided, in accordance with an application of the present invention, a method including:
bringing a support of an electrical-component add-on into contact with a tubular frame of a prosthetic cardiac valve, the electrical-component add-on further including one or more electrical components, which are fixed to the support, and which include an antenna and one or more electrodes; and
attaching the support to the tubular frame of the prosthetic cardiac valve by snappingly engaging snap-fastener first components, defined by the tubular frame, with snap-fastener second components defined by the support.

For some applications, the method further includes, after attaching the support to the tubular frame, implanting the prosthetic cardiac valve and the electrical-component add-on in a body of a patient.

For some applications, the method further includes, after implanting the prosthetic cardiac valve and the electrical-component add-on, wirelessly transmitting energy to the antenna.

For some applications, the snap-fastener second components are shaped so as to define respective studs.

For some applications, the snap-fastener second components are shaped so as to define respective sockets.

For some applications, the support includes support struts, which are shaped so as to define the snap-fastener second components.

For some applications:

the one or more electrical components further include one or more electrical leads, the support struts include electrical insulation, and a portion of the support struts electrically insulates the one or more electrical leads.

For some applications:

the tubular frame defines interconnected stent struts arranged so as to define interconnected stent cells, and attaching the support to the tubular frame includes attaching the support to the tubular frame such that the support struts generally run along a portion of the stent struts.

For some applications, the method further includes, after attaching the support to the tubular frame, radially compressing the tubular frame such that the tubular frame elongates, and the support struts are configured to accommodate elongation of the tubular frame during the radial compression and the elongation of the tubular frame while the support is attached to the tubular frame.

For some applications, the one or more electrical components further include one or more electrical leads.

For some applications, the one or more electrical components further include circuitry.

For some applications, the method further includes:

after attaching the support to the tubular frame, implanting the prosthetic cardiac valve and the electrical-component add-on in a body of a patient; and thereafter, wirelessly transmitting energy to the antenna and activating the circuitry to pace to the heart using at least one of the one or more electrodes.

For some applications, the one or more electrical components further include one or more electrical leads that electrically couple the one or more electrodes to the circuitry.

For some applications, attaching the support to the tubular frame includes elongating the support, in at least one direction, by at least 2% of an initial length of the support, measured in the at least one direction while the support is unconstrained.

For some applications, attaching the support to the tubular frame includes attaching the support to the tubular frame such that the support surrounds less than 360 degrees of the tubular frame, with respect to a longitudinal axis of the tubular frame.

For some applications, the support is rotationally asymmetric when unconstrained.

For some applications:

the tubular frame defines interconnected stent struts arranged so as to define interconnected stent cells, and attaching the support to the tubular frame includes using the snap-fastener second components to attach the support to one or more proximal stent cells at a proximal end of the tubular frame, and to one or more distal stent cells of the tubular frame at a distal end of the tubular frame.

For some applications, attaching the support to the tubular frame includes using the snap-fastener second components to attach the support to two or more distal stent cells of the tubular frame at the distal end of the tubular frame.

For some applications, attaching the support to the tubular frame includes using the snap-fastener second components to attach the support to three or more distal stent cells of the tubular frame at the distal end of the tubular frame.

For some applications, attaching the support to the tubular frame includes using the snap-fastener second components to attach the support to no more than ten distal stent cells of the tubular frame at the distal end of the tubular frame.

For some applications, attaching the support to the tubular frame includes using the snap-fastener second components to attach the support to no more than 50% of the distal stent cells of the tubular frame.

For some applications:

the two or more distal stent cells include first and second distal stent cells, which are separated from each other around the tubular frame by at least one intervening third distal stent cell, and attaching the support to the tubular frame includes using the snap-fastener second components to attach the support to the first and the second distal stent cells at the distal end of the tubular frame.

For some applications, attaching the support to the tubular frame includes using the snap-fastener second components to attach the support to two or more proximal stent cells at the proximal end of the tubular frame.

For some applications, the two or more proximal stent cells are adjacent to each other around the tubular frame.

For some applications, attaching the support to the tubular frame includes attaching the support to the tubular frame to a radially-outward surface of the tubular frame.

For some applications, the prosthetic cardiac valve includes a plurality of prosthetic leaflets coupled to the tubular frame so as to allow blood flow in a proximal downstream direction and inhibit blood flow in a distal upstream direction.

For some applications:

the method further includes, after attaching the support to the tubular frame:

radially compressing the tubular frame; and thereafter, implanting the prosthetic cardiac valve and the electrical-component add-on in a body of a patient, and the method does not include inserting the radially-compressed tubular frame and the support into a sterile package after radially compressing the tubular frame.

For some applications:

the method further includes, after attaching the support to the tubular frame, radially compressing the tubular frame, and the method does not include inserting the radially-compressed tubular frame and the support into a sterile package after attaching the support to the tubular frame.

For some applications:

the electrical-component add-on is sterile and is contained within a first sterile package, the prosthetic cardiac valve is sterile and is contained within a second sterile package, and the method further includes, before bringing the support of the electrical-component add-on into contact with the tubular frame of the prosthetic cardiac valve:

removing the electrical-component add-on from the first sterile package; and removing the prosthetic cardiac valve from the second sterile package.

There is yet additionally provided, in accordance with an application of the present invention, an apparatus including an electrical-component add-on for attachment to a prosthetic cardiac valve including a tubular frame defining interconnected stent struts arranged so as to define interconnected stent cells, the cardiac valve further including a skirt including flexible sheeting and covering a portion of the tubular frame, the electrical-component add-on including:

a support, including a flexible sheet; and one or more electrical components, which are fixed to the support, and which include an antenna and one or more electrodes, wherein the apparatus further includes a plurality of fasteners, which are configured to fasten the flexible sheet of the electrical-component add-on to the prosthetic cardiac valve.

For some applications, the fasteners are configured to fasten by undergoing plastic deformation.

For some applications, the fasteners include staples.

For some applications, at least a portion of the fasteners are configured to fasten the flexible sheet of the electrical-component add-on to the skirt of the prosthetic cardiac valve.

For some applications, the flexible sheet is stretchable.

For some applications, the plurality of fasteners include two-ten fasteners.

For some applications, the one or more electrical components further include one or more electrical leads.

For some applications, the one or more electrical components further include circuitry.

For some applications, the circuitry is configured to pace a heart of a patient using at least one of the one or more electrodes.

For some applications, the one or more electrical components further include one or more electrical leads that electrically couple the one or more electrodes to the circuitry.

For some applications, the flexible sheet, when unconstrained in a non-stretched state, has a surface area of 720-1000 mm2.

For some applications, the flexible sheet, when unconstrained in a non-stretched state, has a greatest dimension of 45-65 mm.

For some applications, the flexible sheet is configured such that when the support is attached to the prosthetic cardiac valve, the flexible sheet surrounds less than 360 degrees of the prosthetic cardiac valve, with respect to a longitudinal axis of the tubular frame.

For some applications, the flexible sheet is rotationally asymmetric when unconstrained.

For some applications, the apparatus further includes a sterile package, and the electrical-component add-on is sterile and is contained within the sterile package, which does not also contain the prosthetic cardiac valve.

For some applications:

the flexible sheet is shaped so as to define a flap, which is configured to be folded over a portion of the stent struts of the tubular frame, such that the flap is disposed radially inside the tubular frame alongside a portion of the flexible sheet disposed radially outside the tubular frame, and a portion of the fasteners are configured to attach the electrical-component add-on to the prosthetic cardiac valve by fastening the portion of the flexible sheet to the flap.

For some applications, the flexible sheet is shaped so as to define the flap at a proximal end portion of the flexible sheet.

For some applications, a prosthetic cardiac valve system is provided that includes the apparatus and further includes the prosthetic cardiac valve.

For some applications, the prosthetic cardiac valve includes a plurality of prosthetic leaflets coupled to the tubular frame so as to allow blood flow in a proximal downstream direction and inhibit blood flow in a distal upstream direction.

For some applications:

the flexible sheet is stretchable, the tubular frame is radially compressible, and is configured to elongate when radially compressed, and the stretchable flexible sheet is configured to accommodate elongation of the tubular frame during radial compression and the elongation of the tubular frame while the support is attached to the prosthetic cardiac valve.

For some applications, the prosthetic cardiac valve system further includes first and second sterile packages, the electrical-component add-on is sterile and is contained within the first sterile package, and the prosthetic cardiac valve is sterile and is contained within the second sterile package.

There is also provided, in accordance with an application of the present invention, a method including:

bringing a support of an electrical-component add-on into contact with a prosthetic cardiac valve, the support including a flexible sheet, and the electrical-component add-on further including one or more electrical components, which are fixed to the support, and which include an antenna and one or more electrodes; and using a plurality of fasteners, fastening the flexible sheet of the electrical-component add-on to the prosthetic cardiac valve.

For some applications, the method further includes, after fastening the electrical-component add-on to the prosthetic cardiac valve, implanting the prosthetic cardiac valve and the electrical-component add-on in a body of a patient.

For some applications, the method further includes, after implanting the prosthetic cardiac valve and the electrical-component add-on, wirelessly transmitting energy to the antenna.

For some applications, the fasteners are configured to fasten by undergoing plastic deformation.

For some applications, the fasteners include staples, and fastening the flexible sheet of the electrical-component add-on to the prosthetic cardiac valve includes stapling the flexible sheet of the electrical-component add-on to the prosthetic cardiac valve.

For some applications:

the cardiac valve includes a tubular frame and a skirt including flexible sheeting and covering a portion of the tubular frame, and fastening the flexible sheet of the electrical-component add-on to the prosthetic cardiac valve includes using at least a portion of the fasteners to fasten the flexible sheet of the electrical-component add-on to the skirt of the prosthetic cardiac valve.

For some applications, the flexible sheet is stretchable.

For some applications, the one or more electrical components further include one or more electrical leads.

For some applications, the one or more electrical components further include circuitry.

For some applications, the method further includes:

after fastening the flexible sheet of the electrical-component add-on to the prosthetic cardiac valve, implanting the prosthetic cardiac valve and the electrical-component add-on in a body of a patient; and thereafter, wirelessly transmitting energy to the antenna and activating the circuitry to pace to a heart of a patient using at least one of the one or more electrodes.

For some applications, the one or more electrical components further include one or more electrical leads that electrically couple the one or more electrodes to the circuitry.

For some applications, the cardiac valve includes a tubular frame, and fastening the electrical-component add-on to the prosthetic cardiac valve includes fastening the electrical-component add-on to the prosthetic cardiac valve such that the flexible sheet surrounds less than 360 degrees of the prosthetic cardiac valve, with respect to a longitudinal axis of the tubular frame.

For some applications, the flexible sheet is rotationally asymmetric when unconstrained.

For some applications:
the cardiac valve includes a tubular frame that defines interconnected stent struts arranged so as to define interconnected stent cells,
the flexible sheet is shaped so as to define a flap, and
fastening the electrical-component add-on to the prosthetic cardiac valve includes:
folding the flap over a portion of the stent struts of the tubular frame, such that the flap is disposed radially inside the tubular frame alongside a portion of the flexible sheet disposed radially outside the tubular frame; and
using a portion of the fasteners to attach the electrical-component add-on to the prosthetic cardiac valve by fastening the portion of the flexible sheet to the flap.

For some applications, the flexible sheet is shaped so as to define the flap at a proximal end portion of the flexible sheet.

For some applications, the prosthetic cardiac valve includes a tubular frame and a plurality of prosthetic leaflets coupled to the tubular frame so as to allow blood flow in a proximal downstream direction and inhibit blood flow in a distal upstream direction.

For some applications, the cardiac valve includes a tubular frame, the flexible sheet is stretchable, and the method further includes, after attaching the support to the prosthetic cardiac valve, radially compressing the tubular frame such that the tubular frame elongates, the stretchable sheet is configured to accommodate elongation of the tubular frame during the radial compression and the elongation of the tubular frame while the support is attached to the tubular frame.

For some applications:
the cardiac valve includes a tubular frame,
the method further includes, after fastening the flexible sheet of the electrical-component add-on to the prosthetic cardiac valve:
radially compressing the tubular frame; and
thereafter, implanting the prosthetic cardiac valve and the electrical-component add-on in a body of a patient, and
the method does not include inserting the radially-compressed tubular frame and the support into a sterile package after radially compressing the tubular frame.

For some applications:
the cardiac valve includes a tubular frame,
the method further includes, after attaching the support to the tubular frame, radially compressing the tubular frame, and
the method does not include inserting the radially-compressed tubular frame and the support into a sterile package after fastening the flexible sheet of the electrical-component add-on to the prosthetic cardiac valve.

For some applications:
the cardiac valve includes a tubular frame,
the electrical-component add-on is sterile and is contained within a first sterile package,
the prosthetic cardiac valve is sterile and is contained within a second sterile package, and
the method further includes, before bringing the support of the electrical-component add-on into contact with the tubular frame of the prosthetic cardiac valve:
removing the electrical-component add-on from the first sterile package; and
removing the prosthetic cardiac valve from the second sterile package.

There is further provided, in accordance with an application of the present invention, an electrical-component add-on for use with a prosthetic cardiac valve including a tubular frame, the electrical-component add-on including:
a support, which is (a) configured to assume delivery and deployed configurations, (b) configured to be positioned above, at, or below an annulus of a native cardiac valve of a heart, and (c) shaped as a ring when in the deployed configuration, so as to receive the tubular frame of the prosthetic cardiac valve within the support; and
one or more electrical components, which are supported by the support, and which include an antenna and one or more electrodes.

For some applications, the one or more electrical components further include one or more electrical leads.

For some applications, the one or more electrical components further include circuitry.

For some applications, the circuitry is configured to pace the heart using at least one of the one or more electrodes.

For some applications, the circuitry includes a PCB.

For some applications, the one or more electrical components further include one or more electrical leads that electrically couple the one or more electrodes to the circuitry.

For some applications, the apparatus further includes one or more elongate PCBs with which the one or more electrical leads are integral.

For some applications, the support is configured to be positioned below the annulus.

For some applications, the support is configured to be positioned at the annulus.

For some applications, the antenna includes at least one prosthetic-valve coil that is not coaxial with the support when the support is in the deployed configuration.

For some applications, the electrical-component add-on does not include valve leaflets.

For some applications, the support is shaped so as to surround a lumen when in the deployed configuration, and the lumen is free of the one or more electrical components.

For some applications, when the support is in the deployed configuration:
the support defines a central longitudinal axis and has proximal and distal ends, and
the one or more electrodes are disposed axially between an axial location 10 mm proximal to the proximal end and an axial location 10 mm distal to the distal end.

For some applications, when the support is in the deployed configuration, the one or more electrodes are disposed axially between the proximal and the distal ends of the support.

For some applications, when the support is in the deployed configuration:

the support defines a central longitudinal axis and has proximal and distal ends, and the one or more electrical components are disposed axially between an axial location 10 mm proximal to the proximal end and an axial location 10 mm distal to the distal end.

For some applications, the support is configured such that radial expansion of the tubular frame within the support radially expands the support and anchors the support in place above, at, or below the annulus.

For some applications, a height of the support, when in the deployed configuration, is 5-15 mm.

For some applications, an outer diameter of the support, when in the deployed configuration, is 19-35 mm.

For some applications, a height of the support, when in the deployed configuration, is 5-15 mm.

For some applications, the support includes a tubular stent including interconnected stent struts.

For some applications, the interconnected stent struts are arranged so as to define interconnected stent cells.

For some applications, the interconnected stent struts are arranged so as to define exactly one or exactly two rows of the interconnected stent cells.

For some applications, the support includes a wire having a shape memory that causes the wire to assume a ring shape when the support is in the deployed configuration.

For some applications, the wire, when having the ring shape, defines more than one turn and fewer than five turns when the support is in the deployed configuration.

For some applications:

the support includes an electrical-component mount that assumes an arcuate shape when the support is in the deployed configuration, the arcuate shape having an arc length of less than 360 degrees, and the one or more electrodes are fixed to the electrical-component mount.

For some applications, the arc length is at least 180 degrees when the support is in the deployed configuration.

For some applications, the wire includes a metal and electrical-component mount includes a polymer.

For some applications:

the one or more electrical components further include circuitry and one or more electrical leads that electrically couple the one or more electrodes to the circuitry, and the one or more electrical leads are integral with electrical-component mount.

For some applications, the electrical-component mount includes an elongate PCB.

For some applications, the electrical-component add-on further includes a sterile package, and the electrical-component add-on is sterile and is contained within the sterile package, which does not also contain the prosthetic cardiac valve.

For some applications, a prosthetic cardiac valve system is provided that includes the electrical-component add-on and further includes a delivery system, which includes one or more elongate deployment members that are reversibly coupled to the support and configured, while reversibly coupled to the support, to hold the support above, at, or below the annulus, while the tubular frame of the prosthetic cardiac valve is unconnected to the support.

For some applications, the support is shaped, when in the deployed configuration, so as to receive the tubular frame of the prosthetic cardiac valve within the support while the one or more elongate deployment members are reversibly coupled to the support.

For some applications, the prosthetic cardiac valve system further includes the prosthetic cardiac valve.

For some applications, a prosthetic cardiac valve system is provided that includes electrical-component add-on and further includes the prosthetic cardiac valve.

For some applications, the prosthetic cardiac valve includes a plurality of prosthetic leaflets coupled to the tubular frame so as to allow blood flow in a proximal downstream direction and inhibit blood flow in a distal upstream direction.

For some applications, the prosthetic cardiac valve system further includes first and second sterile packages, the electrical-component add-on is sterile and is contained within the first sterile package, and the prosthetic cardiac valve is sterile and is contained within the second sterile package.

There is still further provided, in accordance with an application of the present invention, a method including:

advancing a support of an electrical-component add-on to a native cardiac valve of a heart while the support is in a delivery configuration, the electrical-component add-on further including one or more electrical components, which are supported by the support, and which include an antenna and one or more electrodes;

positioning the support above, at, or below an annulus of the native cardiac valve and transitioning the support from the delivery configuration to a deployed configuration in which the support is shaped as a ring; and thereafter, placing a tubular frame of a prosthetic cardiac valve within the support.

For some applications, the one or more electrical components further include one or more electrical leads.

For some applications, the one or more electrical components further include circuitry.

For some applications, the method further includes, after positioning the support above, at, or below the annulus, wirelessly transmitting energy to the antenna and activating the circuitry to pace to the heart using at least one of the one or more electrodes.

For some applications, the circuitry includes a PCB.

For some applications, the one or more electrical components further include one or more electrical leads that electrically couple the one or more electrodes to the circuitry.

For some applications, the electrical-component add-on further includes one or more elongate PCBs with which the one or more electrical leads are integral.

For some applications, positioning the support includes positioning the support below the annulus.

For some applications, positioning the support includes positioning the support at the annulus.

For some applications, the antenna includes at least one prosthetic-valve coil that is not coaxial with the support when the support is in the deployed configuration.

For some applications, the electrical-component add-on does not include valve leaflets.

For some applications, the support is shaped so as to surround a lumen when in the deployed configuration, and the lumen is free of the one or more electrical components.

For some applications, when the support is in the deployed configuration:

the support defines a central longitudinal axis and has proximal and distal ends, and the one or more electrodes are disposed axially between an axial location 10 mm proximal to the proximal end and an axial location 10 mm distal to the distal end.

For some applications, when the support is in the deployed configuration, the one or more electrodes are disposed axially between the proximal and the distal ends of the support.

For some applications, when the support is in the deployed configuration:

the support defines a central longitudinal axis and has proximal and distal ends, and the one or more electrical components are disposed axially between an axial location 10 mm proximal to the proximal end and an axial location 10 mm distal to the distal end.

For some applications, placing the tubular frame within the support includes radially expanding the tubular frame within the support to radially expand the support and anchor the support in place above, at, or below the annulus.

For some applications, a height of the support, when in the deployed configuration, is 5-15 mm.

For some applications, an outer diameter of the support, when in the deployed configuration, is 19-35 mm.

For some applications, a height of the support, when in the deployed configuration, is 5-15 mm.

For some applications, the support includes a tubular stent including interconnected stent struts.

For some applications, the interconnected stent struts are arranged so as to define interconnected stent cells.

For some applications, the interconnected stent struts are arranged so as to define exactly one or exactly two rows of the interconnected stent cells.

For some applications, the support includes a wire having a shape memory that causes the wire to assume a ring shape when the support is in the deployed configuration.

For some applications, the wire, when having the ring shape, defines more than one turn and fewer than five turns when the support is in the deployed configuration.

For some applications:

the support includes an electrical-component mount that assumes an arcuate shape when the support is in the deployed configuration, the arcuate shape having an arc length of less than 360 degrees, and the one or more electrodes are fixed to electrical-component mount.

For some applications, the arc length is at least 180 when the support is in the deployed configuration.

For some applications, the wire includes a metal and electrical-component mount includes a polymer.

For some applications:

the one or more electrical components further include circuitry and one or more electrical leads that electrically couple the one or more electrodes to the circuitry, and the one or more electrical leads are integral with electrical-component mount.

For some applications, electrical-component mount includes an elongate PCB.

For some applications, positioning the support above, at, or below the annulus includes using one or more elongate deployment members of a delivery system to hold the support above, at, or below the annulus while the one or more elongate deployment members are reversibly coupled to the support, and while the tubular frame of the prosthetic cardiac valve is unconnected to the support.

For some applications:

placing the tubular frame within the support includes placing the tubular frame within the support while the one or more elongate deployment members are reversibly coupled to the support, and the method further includes decoupling the one or more elongate deployment members from the support after placing the tubular frame within the support.

For some applications, the prosthetic cardiac valve includes a plurality of prosthetic leaflets coupled to the tubular frame so as to allow blood flow in a proximal downstream direction and inhibit blood flow in a distal upstream direction.

For some applications, the method further includes, after positioning the support above, at, or below the annulus, wirelessly transmitting energy to the antenna.

The present invention will be more fully understood from the following detailed description of embodiments thereof, taken together with the drawings, in which:

BRIEF DESCRIPTION OF THE DRAWINGS

FIGS. 20A-C are schematic illustrations of several views of an electrical-component add-on of the prosthetic cardiac valve system of FIGS. 18 and 19 in a deployed configuration, in accordance with an application of the present invention;

DETAILED DESCRIPTION OF APPLICATIONS

Figures 1, 2:
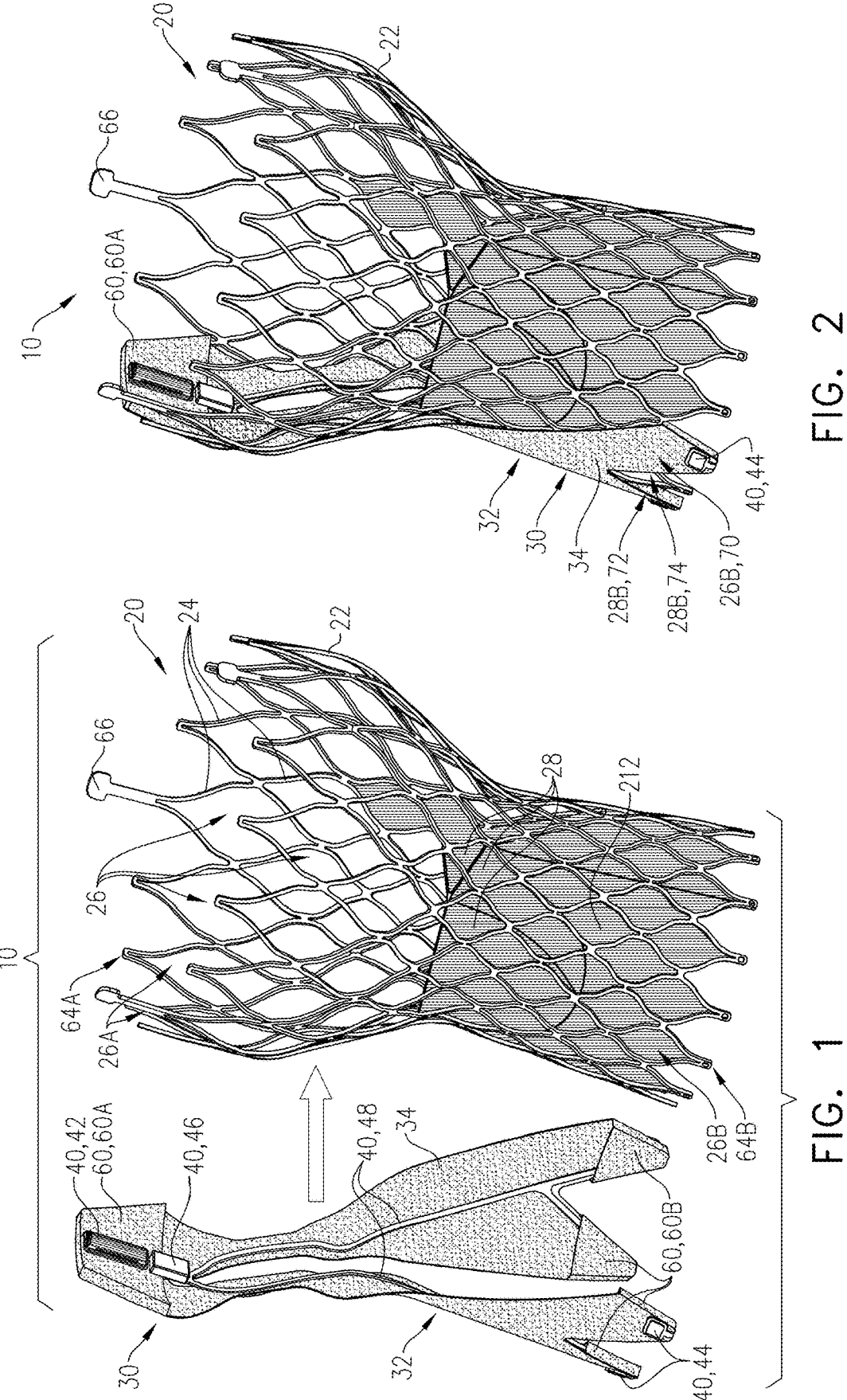
FIG. 1 is a schematic illustration of a prosthetic cardiac valve system, in accordance with an application of the present invention.
FIG. 2 is another schematic illustration of the prosthetic cardiac valve system of FIG. 1, in accordance with an application of the present invention.

Reference is made to FIGS. 1 and 2, which are schematic illustrations of a prosthetic cardiac valve system 10, in accordance with an application of the present invention. Prosthetic cardiac valve system 10 comprises a prosthetic cardiac valve 20 and an electrical-component add-on 30. Prosthetic cardiac valve system 10 may comprise additional elements, for example as described hereinbelow with reference to FIG. 13.

For some applications, prosthetic cardiac valve 20 comprises a prosthetic aortic valve, such as shown in the figures. For other applications, prosthetic cardiac valve 20 comprises a prosthetic atrioventricular valve, i.e., a prosthetic mitral valve or a prosthetic tricuspid valve (configuration not shown); for example, the prosthetic atrioventricular valve may implement any of the techniques described with reference to FIG. 9 of International Appl. No. PCT/IL2024/050830, filed Aug. 18, 2024, which published as PCT Publication WO 2025/041129 to Gross et al. and which is assigned to the assignee of the present application and incorporated herein by reference.

Prosthetic cardiac valve 20 comprises a tubular frame 22 defining interconnected stent struts 24 arranged so as to define interconnected stent cells 26 (labeled in FIG. 1). Tubular frame 22 is typically self-expanding, and may be formed by laser cutting or etching a metal alloy tube comprising, for example, stainless steel or a shape memory material such as Nitinol. Optionally, interconnected stent cells 26 are generally diamond-shaped, such as shown in the drawings.

Typically, prosthetic cardiac valve 20 comprises a plurality of prosthetic leaflets 28 (labeled in FIGS. 1 and 4C) coupled to tubular frame 22 so as to allow blood flow in a proximal downstream direction and inhibit blood flow in a distal upstream direction. (As used herein, the terms "distal" and "proximal" correspond to "upstream" and "downstream," respectively, in configurations in which prosthetic cardiac valve 20 comprises prosthetic leaflets 28.) Typically, adjoining pairs of prosthetic leaflets 28 are attached to one another at their lateral ends to form commissures, with free edges of the prosthetic leaflets forming coaptation edges that meet one another. Prosthetic leaflets 28 typically comprise a sheet of animal pericardial tissue, such as porcine pericardial tissue, or synthetic or polymeric material.

The features, including the geometry, stent structure, and leaflet arrangement, of prosthetic cardiac valve 20 shown in FIGS. 1 and 2 (and other figures) are by way of example and not limitation; optionally, prosthetic cardiac valve 20 may implement the features of any other prosthetic cardiac valves known in the art. Optionally, prosthetic cardiac valve 20 may implement any of the features described in the patents and patent application publications incorporated by reference hereinbelow.

Electrical-component add-on 30 is configured to be easily attached to tubular frame 22 of prosthetic cardiac valve 20, such as by a healthcare worker. FIG. 1 shows prosthetic cardiac valve system 10 prior to attachment of electrical-component add-on 30 to tubular frame 22, and FIG. 2 shows prosthetic cardiac valve system 10 after attachment of electrical-component add-on 30 to tubular frame 22. Typically, a healthcare worker (e.g., a technician) attaches electrical-component add-on 30 to tubular frame 22 during or shortly before an implantation procedure in which prosthetic cardiac valve 20 and attached electrical-component add-on 30 are implanted in a body of a patient. For example, electrical-component add-on 30 may be attached to tubular frame 22 in an operating room or a cath lab.

Reference is still made to FIGS. 1 and 2, and is further made to FIGS. 3A-D, which are schematic illustrations of several views of electrical-component add-on 30.

Figures 4A, 4B, 4C, 5:
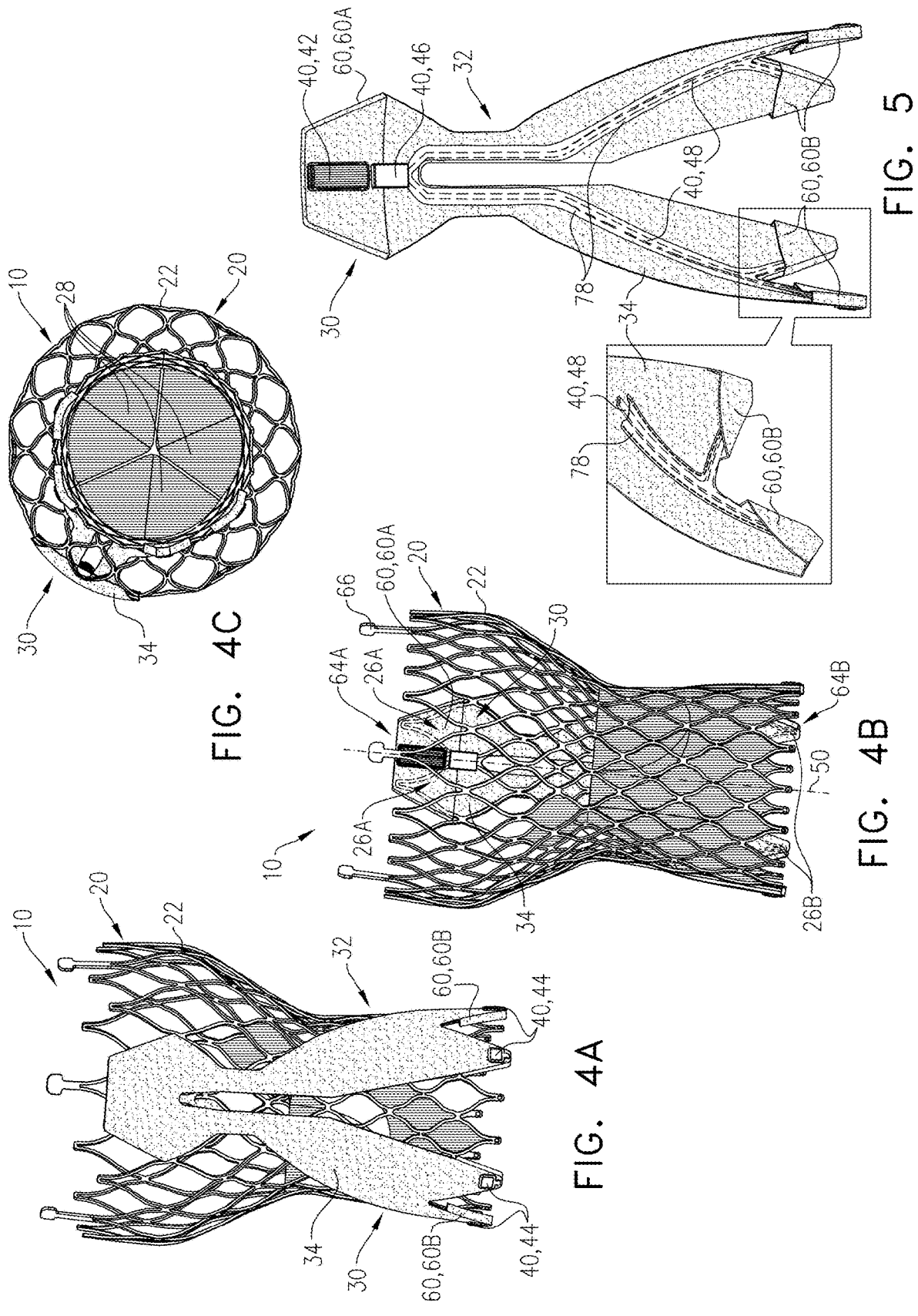
FIGS. 4A-C are schematic illustrations of several views of the prosthetic cardiac valve system of FIGS. 1 and 2 after attachment of the electrical-component add-on to a tubular frame of a prosthetic cardiac valve of the prosthetic cardiac valve system, in accordance with an application of the present invention.
FIG. 5 is a schematic illustration of an alternative configuration of an electrical-component add-on of the prosthetic cardiac valve system of FIGS. 1 and 2, in accordance with an application of the present invention.

Reference is still further made to FIGS. 4A-C, which are schematic illustrations of several views of prosthetic cardiac valve system 10 after attachment of electrical-component add-on 30 to tubular frame 22.

In some applications of the present invention, electrical-component add-on 30 comprises:

a support 32, comprising a stretchable sheet 34 (which is typically elastic), which is shaped so as to facilitate attachment of support 32 to tubular frame 22 of prosthetic cardiac valve 20 by stretching of stretchable sheet 34; and one or more electrical components 40, which are fixed to support 32.

Typically, stretchable sheet 34 is shaped so as to facilitate the attachment of support 32 to tubular frame 22 without piercing of stretchable sheet 34.

Typically, stretchable sheet 34 is shaped so as to facilitate the attachment of support 32 to tubular frame 22 without stitching of stretchable sheet 34.

For some applications, stretchable sheet 34 is shaped so as to facilitate the attachment of support 32 to a radially-outward surface of tubular frame 22, such as shown in FIGS. 1-4C. For some of these applications, stretchable sheet 34 is shaped so as to facilitate the attachment of support 32 to the radially-outward surface of tubular frame 22 such that stretchable sheet 34 at least partially covers at least three, e.g., at least five stent cells 26.

For some applications, stretchable sheet 34, when unconstrained in a non-stretched state, has:

a surface area of at least 720 mm2, no more than 1000 mm2, and/or 720-1000 mm2, and/or a greatest dimension of at least 45 mm, no more than 65 mm, and/or 45-65 mm (for example, the greatest dimension may be a length, measured in a proximal-to-distal direction).

Typically, stretchable sheet 34 comprises a stretchable fabric, e.g., a stretch knit, e.g., comprising a polymer (e.g., a polyester), such as Polyethylene terephthalate (PET). Alternatively, stretchable sheet 34 comprises another stretchable material, such as silicone.

For some applications, stretchable sheet 34 has an elastic capacity of at least 20 cN/Tex, no more than 60 cN/Tex, and/or 20-60 cN/Tex. (As is known in the fabric arts, the centi Newton/Tex (cN/Tex) is a unit for expressing the elastic capacity of a textile, which can be measured with a dynamometer. The elastic limit of a material is defined by the force in cN/Tex that it is able to support and then return to its initial shape, without deformation.)

For some applications, stretchable sheet 34 has a thickness of 30-700 microns, e.g., 30-100 microns or 400-700 microns.

For some applications, stretchable sheet is elongatable, in at least one direction, by at least 10%, e.g., at least 20%, and/or no more than 50%, e.g., no more than 40% of an initial length of stretchable sheet 34, measured in the at least one direction while stretchable sheet 34 is unconstrained.

The one or more electrical components 40 typically comprise one or more of the following (labeled in FIGS. 3A-D):

an antenna 42 (which typically comprises one or more prosthetic-valve coils);

one or more electrodes 44;

circuitry 46 (e.g., comprising a PCB and/or electronic components, e.g., a processor); and/or one or more electrical leads 48 (which may electrically couple the one or more electrodes 44 to circuitry 46, if provided).

For some applications, circuitry 46 is configured to apply pacing to the heart using the one or more electrodes 44, optionally using any of the features described in the patents and patent application publications incorporated by reference hereinbelow. For example, the pacing may be applied temporarily for up to several weeks after implantation of prosthetic cardiac valve 20 with electrical-component add-on 30 attached thereto (e.g., up to one month after implantation), typically using an external control unit to continuously provide power, such as external control unit 300, described hereinbelow with reference to FIG. 13.

Alternatively, for some applications, the pacing is applied longer-term, in which case prosthetic cardiac valve system 10 may comprise an energy storage module, e.g., comprising a battery. For example, prosthetic cardiac valve 20 may further comprise the energy storage module, e.g., comprising a battery, which may be periodically charged using the external control unit, which may obviate the need for the patient to constantly wear an external energy transmitter. Alternatively or additionally, for example, prosthetic cardiac valve system 10 may comprise an implantable energy storage module, e.g., comprising a battery (e.g., a rechargeable battery); for example, the energy storage module may be implantable subcutaneously. The implantable energy storage unit may provide power to prosthetic cardiac valve 20 either wirelessly and/or wiredly. For example, the pacing may comprise ongoing sensing of a native electrical signal of the heart and deliverance of electrical stimulus in cases in which the native signal is unsatisfactory for timely ventricular contraction ("VVI pacing").

Further alternatively or additionally, for some applications, circuitry 46 is configured to apply rapid pacing during an invasive structural heart procedure, such as an implantation procedure, such as a TAVR procedure, or a TAVR-in-TAVR procedure in which the first TAVR comprises prosthetic aortic valve 20.

For some applications, prosthetic cardiac valve system 10 is configured to sense an electrocardiography (ECG) of the patient's heart. Circuitry 46 may be configured to sense the ECG, or separate circuitry may be provided for sensing the ECG. The ECG sensing may be performed using all or a subset of electrodes 44 and/or one or more separate electrodes may be provided for performing the ECG sensing.

Optionally, the one or more electrical components 40 of electrical-component add-on 30 may implement any of the features described in the patents and patent application publications incorporated by reference hereinbelow.

For some applications, stretchable sheet 34 is configured such that when support 32 is attached to tubular frame 22, stretchable sheet 34 surrounds less than 360 degrees of tubular frame 22, with respect to a longitudinal axis 50 of tubular frame 22 (labeled in FIG. 4B).

For some applications, stretchable sheet 34 is rotationally asymmetric when unconstrained, such as shown in FIGS. 1-4C. When unconstrained, support 32 may be configured to have the shape shown in FIGS. 1 and 3A-D, or may be flatter, and only assume its final shape when attached to tubular frame 22, such as shown in FIGS. 2 and 4A-C.

For some applications, stretchable sheet 34 is shaped so as to define one or more pockets 60, which are configured to facilitate the attachment of support 32 to tubular frame 22. For some of these applications, the one or more pockets 60 include a proximal pocket 60A and a distal pocket 60B.

Figures 3A, 3B, 3C, 3D:
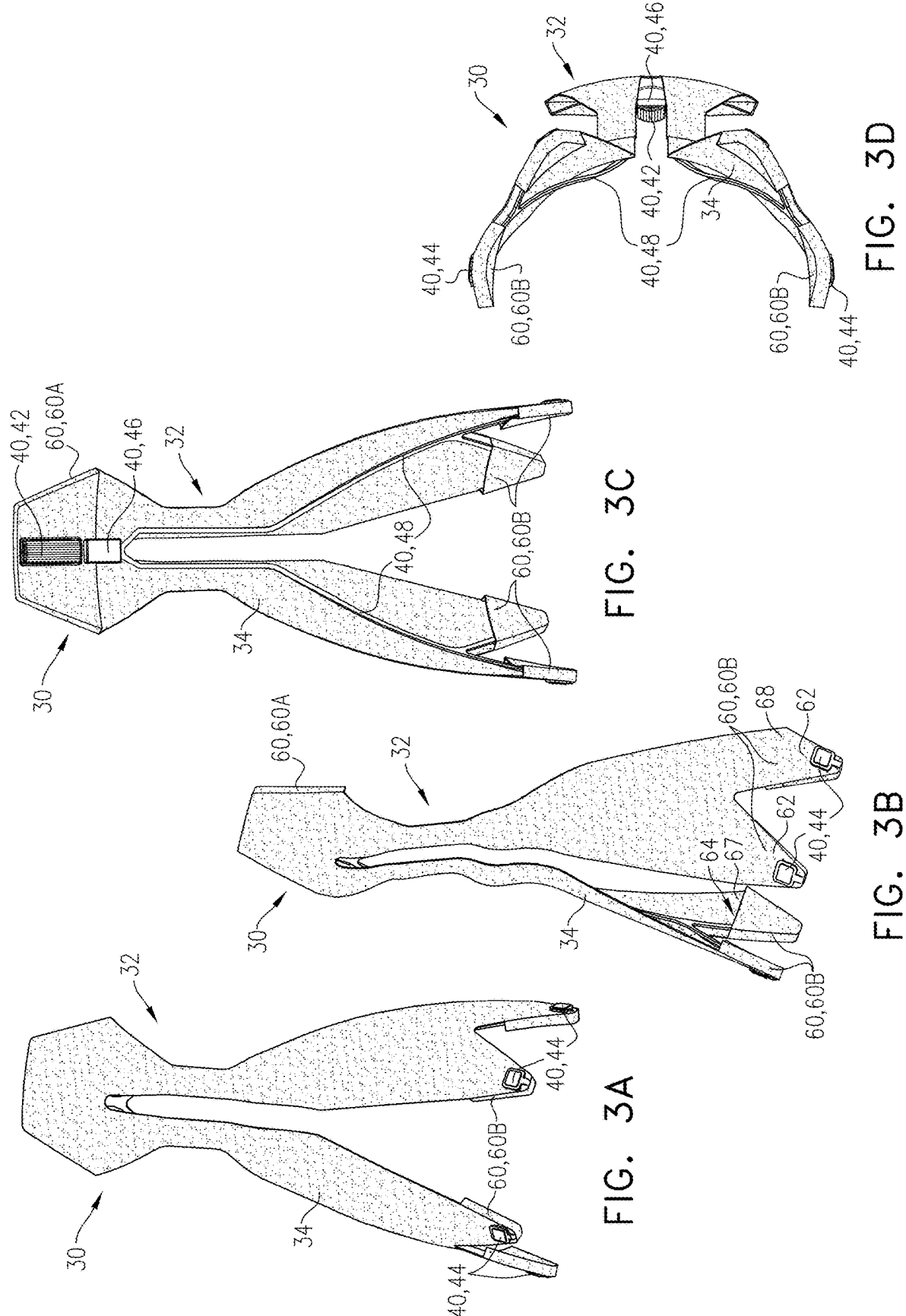
FIGS. 3A-D are schematic illustrations of several views of an electrical-component add-on of the prosthetic cardiac valve system of FIGS. 1 and 2, in accordance with an application of the present invention.

For some applications, as shown in many of the figures and labeled in FIG. 3B, one of the one or more electrodes 44 is fixed to an external surface 62 of the distal pocket 60B. For some of these applications:

the distal pocket 60B is shaped to define a pocket opening 64 on a first surface 67 of stretchable sheet 34 (first surface 67 is a radially inner surface of stretchable sheet 34 after stretchable sheet 34 is attached to tubular frame 22 of prosthetic cardiac valve 20), and wherein external surface 62 of the distal pocket 60B is defined by a second surface 68 of stretchable sheet 34 opposite first surface 67 of stretchable sheet 34 (second surface 68 is a radially outer surface of stretchable sheet 34 after stretchable sheet 34 is attached to tubular frame 22 of prosthetic cardiac valve 20).

Alternatively or additionally, for some applications, the one or more electrical components 40 further comprise circuitry 46, which is fixed to proximal pocket 60A, such as shown, for example, in FIG. 3C.

For some applications, the one or more pockets 60 include two or more distal pockets 60B (two distal pockets 60B are shown in FIGS. 1-4C). Alternatively or additionally, for some applications, the one or more pockets 60 include exactly one proximal pocket 60A, such as shown in FIGS. 1-4C. For example, stretchable sheet 34 may be shaped so as to define exactly one proximal pocket 60A and two or more distal pockets 60B.

For some applications, stretchable sheet 34 is shaped to facilitate the attachment of support 32 to one or more proximal stent cells 26A at a proximal end 64A of tubular frame 22 (labeled in FIGS. 1 and 4B), and to one or more distal stent cells 26B of tubular frame 22 at a distal end 64B of tubular frame 22 (also labeled in FIGS. 1 and 4B). Tubular frame 22 may optionally comprise one or more delivery-tool-coupling tabs 66, which are configured to removably couple tubular frame 22, and thus prosthetic cardiac valve 20, to a delivery system 18, e.g., to a delivery shaft of delivery system 18, such as described hereinbelow with reference to FIG. 13. The one or more delivery-tool-coupling tabs 66 typically are disposed proximal to proximal end 64A of tubular frame 22 (such as shown), or distal to distal end 64B of tubular frame 22 (configuration not shown).

For some of these applications, stretchable sheet 34 is shaped so as to define at least:

proximal pocket 60A, which is shaped to receive the one or more proximal stent cells 26A, so as to facilitate the attachment of support 32 to the one or more proximal stent cells 26A at proximal end 64A of tubular frame 22, and a distal pocket 60B, which is shaped to receive the one or more distal stent cells 26B of tubular frame 22, so as to facilitate the attachment of support 32 to the one or more distal stent cells 26B at distal end 64B of tubular frame 22.

For some applications (whether or not stretchable sheet 34 is shaped so as to define any pockets 60), stretchable sheet 34 is shaped to facilitate the attachment of support 32 to two or more distal stent cells 26B of tubular frame 22 at distal end 64B of tubular frame 22, such as to three or more, e.g., to four or more, distal stent cells 26B, and typically to no more than ten distal stent cells 26B. For some applications, stretchable sheet 34 is shaped to facilitate the attachment of support 32 to no more than 50% of the distal stent cells 26B of tubular frame 22.

For some applications (as labeled in FIG. 2), the two or more distal stent cells 26B include first 70 and second 72 distal stent cells 26B, which are separated from each other around tubular frame 22 by at least one intervening third 74 distal stent cell 26B. Stretchable sheet 34 is shaped to facilitate the attachment of support 32 to the first 70 and the second 72 distal stent cells 26B at distal end 64B of tubular frame 22 (and not necessarily to the intervening third 74 distal stent cell 26B).

For some applications, stretchable sheet 34 is shaped to facilitate the attachment of support 32 to two or more proximal stent cells 26A at proximal end 64A of tubular frame 22. Optionally, the two or more proximal stent cells 26A are adjacent to each other around tubular frame 22, such as shown. Optionally, stretchable sheet 34 is shaped so as to define one or more pockets 60, and a single one of proximal pockets 60A is configured to be attached to the two adjacent proximal stent cells 26A, such as shown in FIGS. 2 and 4A-C (and perhaps best seen in FIG. 4B).

For some applications, tubular frame 22 of prosthetic cardiac valve 20 is radially compressible, and is configured to elongate when radially compressed (i.e., crimped). Stretchable sheet 34 is configured to accommodate elongation of tubular frame 22 during radial compression and the elongation of tubular frame 22 while support 32 is attached to tubular frame 22.

Reference is still made to FIGS. 1-4C, and is further made to FIG. 5, which is a schematic illustration of an alternative configuration of electrical-component add-on 30, in accordance with an application of the present invention. In this configuration, support 32 of electrical-component add-on 30 comprises the above-mentioned one or more electrical leads 48, which are coupled to first surface 67 of stretchable sheet 34 (as described above, first surface 67 is a radially inner surface of stretchable sheet 34 after stretchable sheet 34 is attached to tubular frame 22 of prosthetic cardiac valve 20). Support 32 further comprises one or more stretchable liners 78, which are coupled to first surface 67 of stretchable sheet 34 to cover at least a portion of the one or more electrical leads 48, thereby preventing any entanglement between the one or more electrical leads 48 and stent struts 24 of tubular frame 22 that might otherwise occur.

Reference is made to FIGS. 1-5. For some applications, the one or more electrodes include one or more cathodes and one or more anodes. Optionally, at least one electrode 44, such as a cathode and/or an anode, is disposed at or near (e.g., within 8 mm of) distal end 64B of tubular frame 22, such as shown. Alternatively or additionally, for some applications, at least one electrode 44, such as an anode or a cathode, is disposed on a proximal portion of tubular frame 22, such as (a) a proximal half of tubular frame 22, (b) a portion of tubular frame 22 proximal of prosthetic leaflets 28, and/or (c) a portion of frame defined by a proximal-most two rows of stent cells 26.

Reference is still made to FIGS. 1-5. For some applications, electrical-component add-on 30 further comprises one or more support struts 52, which are coupled to stretchable sheet 34 of support 32, and to which electrical leads 48 are coupled. For some of these applications, the one or more electrical leads 48 are coated with an electrically insulating coating and coupled to at least a portion of support struts 52 (configuration not shown). For other applications, such as shown (and labeled in FIG. 8B for support struts 134), support struts 52 comprise electrical insulation, and a portion of support struts 52 electrically insulates the one or more electrical leads 48. Support struts 52 may implement any of the features of support struts 134 described hereinbelow with reference to FIGS. 6-10, mutatis mutandis, including, but not limited to, the PCB and/or bifurcation features.

For some applications, after sterilization during manufacture, electrical-component add-on 30 is inserted into a sterile package. Thus, electrical-component add-on 30 is sterile and is contained within the sterile package. The sterile package does not also contain the prosthetic cardiac valve 20. Optionally, prosthetic cardiac valve 20 is sterile and is contained within a second sterile package, distinct from the sterile package in which electrical-component add-on 30 is contained.

For some applications, electrical-component add-on 30 comprises two or more supports 32, which comprise respective stretchable sheets 34 and respective electrical components 40. Optionally, the electrical components of the supports 32 are electrically connected to one another.

Reference is still made to FIGS. 1-5. In some applications of the present invention, a method is provided that comprises brining support 32 of electrical-component add-on 30 into contact with tubular frame 22 of prosthetic cardiac valve 20, and attaching support 32 to tubular frame 22 by stretching stretchable sheet 34.

For some applications, the method is performed by a healthcare worker, e.g., a technician (as opposed to a manufacturing worker).

For some applications, attaching support 32 to tubular frame 22 comprises elongating stretchable sheet 34, in at least one direction, by at least 10%, e.g., at least 20%, and/or no more than 50%, e.g., no more than 40% of an initial length of stretchable sheet 34, measured in the at least one direction while stretchable sheet 34 is unconstrained.

For some applications, attaching support 32 to tubular frame 22 comprises attaching support 32 to tubular frame 22 without piercing of stretchable sheet 34.

For some applications, attaching support 32 to tubular frame 22 comprises attaching support 32 to tubular frame 22 without stitching of stretchable sheet 34.

For some applications, the method further comprises, after attaching support 32 to tubular frame 22, radially compressing tubular frame 22 such that tubular frame 22 elongates. Stretchable sheet 34 is configured to accommodate elongation of tubular frame 22 during the radial compression and the elongation of tubular frame 22 while support 32 is attached to tubular frame 22.

For some applications, the method further comprises, after attaching support 32 to tubular frame 22, radially compressing tubular frame 22, and, thereafter, implanting prosthetic cardiac valve 20 and electrical-component add-on 30 in a body of a patient. The method does not comprise inserting the radially-compressed tubular frame 22 and support 32 into a sterile package after radially compressing tubular frame 22.

For some applications, the method further comprises, after attaching support 32 to tubular frame 22, radially compressing tubular frame 22. The method does not comprise inserting the radially-compressed tubular frame 22 and support 32 into a sterile package after attaching support 32 to tubular frame 22.

For some applications, electrical-component add-on 30 is sterile and is contained within a first sterile package, and prosthetic cardiac valve 20 is sterile and is contained within a second sterile package. The method further comprises, before bringing support 32 of electrical-component add-on 30 into contact with tubular frame 22 of prosthetic cardiac valve 20: removing electrical-component add-on 30 from the first sterile package; and removing prosthetic cardiac valve 20 from the second sterile package.

Figures 6, 7:
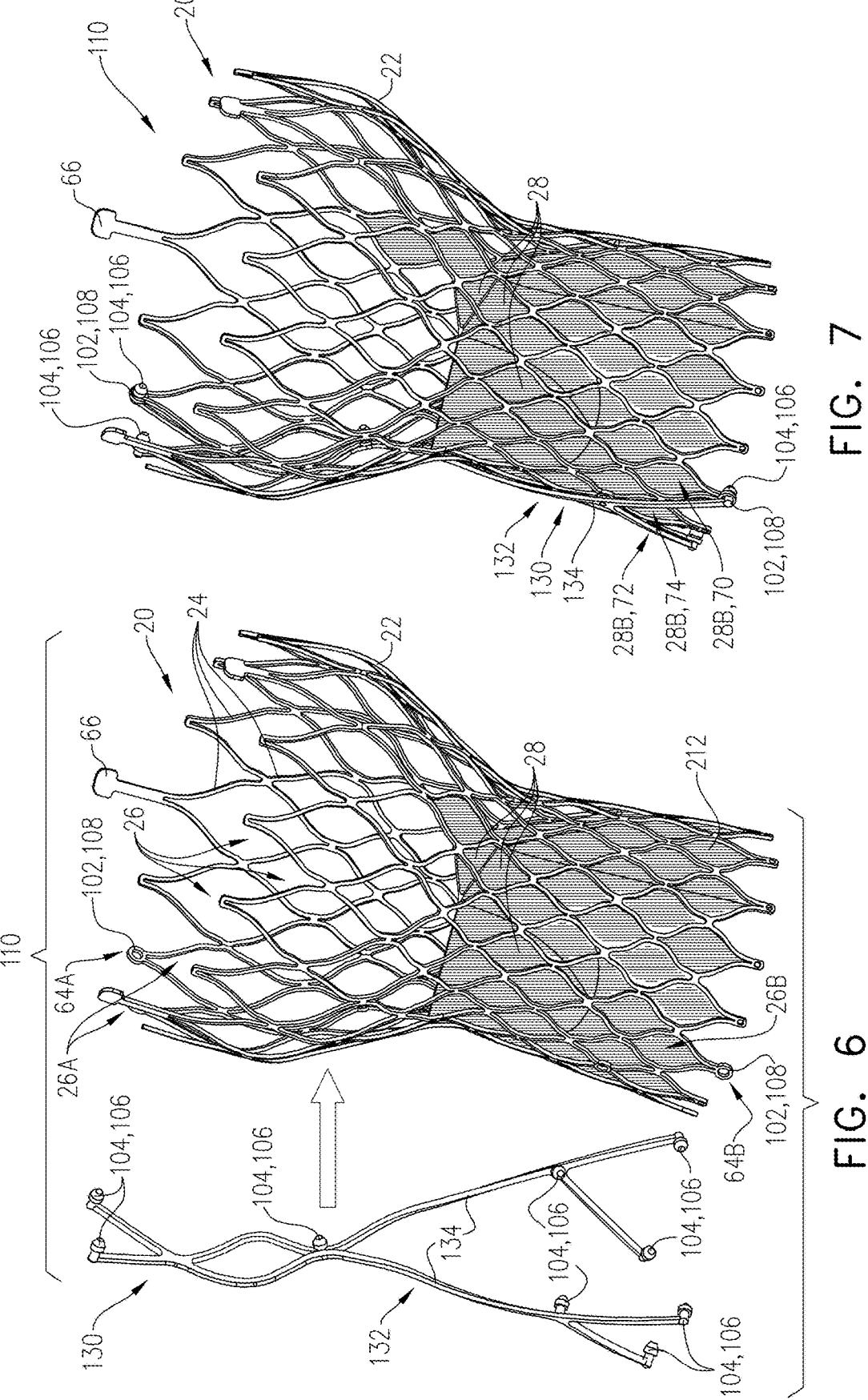
FIG. 6 is a schematic illustrations of another prosthetic cardiac valve system, in accordance with an application of the present invention.
FIG. 7 is another schematic illustration of the prosthetic cardiac valve system of FIG. 6, in accordance with an application of the present invention.

Reference is now made to FIGS. 6 and 7, which are schematic illustrations of a prosthetic cardiac valve system 110, in accordance with an application of the present invention. Prosthetic cardiac valve system 110 comprises prosthetic cardiac valve 20 and an electrical-component add-on 130. Prosthetic cardiac valve system 110 may comprise additional elements, for example as described hereinbelow with reference to FIG. 13. Other than as described hereinbelow, prosthetic cardiac valve 20 may have any of the features thereof described hereinabove with reference to FIGS. 1-4C. Electrical-component add-on 130 may optionally implement any of the features of electrical-component add-on 30, described hereinabove with reference to FIGS. 1-5, mutatis mutandis. Prosthetic cardiac valve system 110 may implement any of the features of prosthetic cardiac valve system 10, described hereinabove with reference to FIGS. 1-5, mutatis mutandis.

Electrical-component add-on 130 is configured to be easily attached to tubular frame 22 of prosthetic cardiac valve 20, such as by a healthcare worker. FIG. 6 shows prosthetic cardiac valve system 110 prior to attachment of electrical-component add-on 130 to tubular frame 22, and FIG. 7 shows prosthetic cardiac valve system 110 after attachment of electrical-component add-on 130 to tubular frame 22. Typically, a healthcare worker attaches electrical-component add-on 130 to tubular frame 22 during or soon before an implantation procedure in which prosthetic cardiac valve 20 and attached electrical-component add-on 130 are implanted in a patient. For example, electrical-component add-on 130 may be attached to tubular frame 22 in an operating room or a cath lab.

Reference is still made to FIGS. 6 and 7, and is further made to FIGS. 8A-D, which are schematic illustrations of several views of electrical-component add-on 130, in accordance with an application of the present invention.

Figures 9A, 9B, 9C:
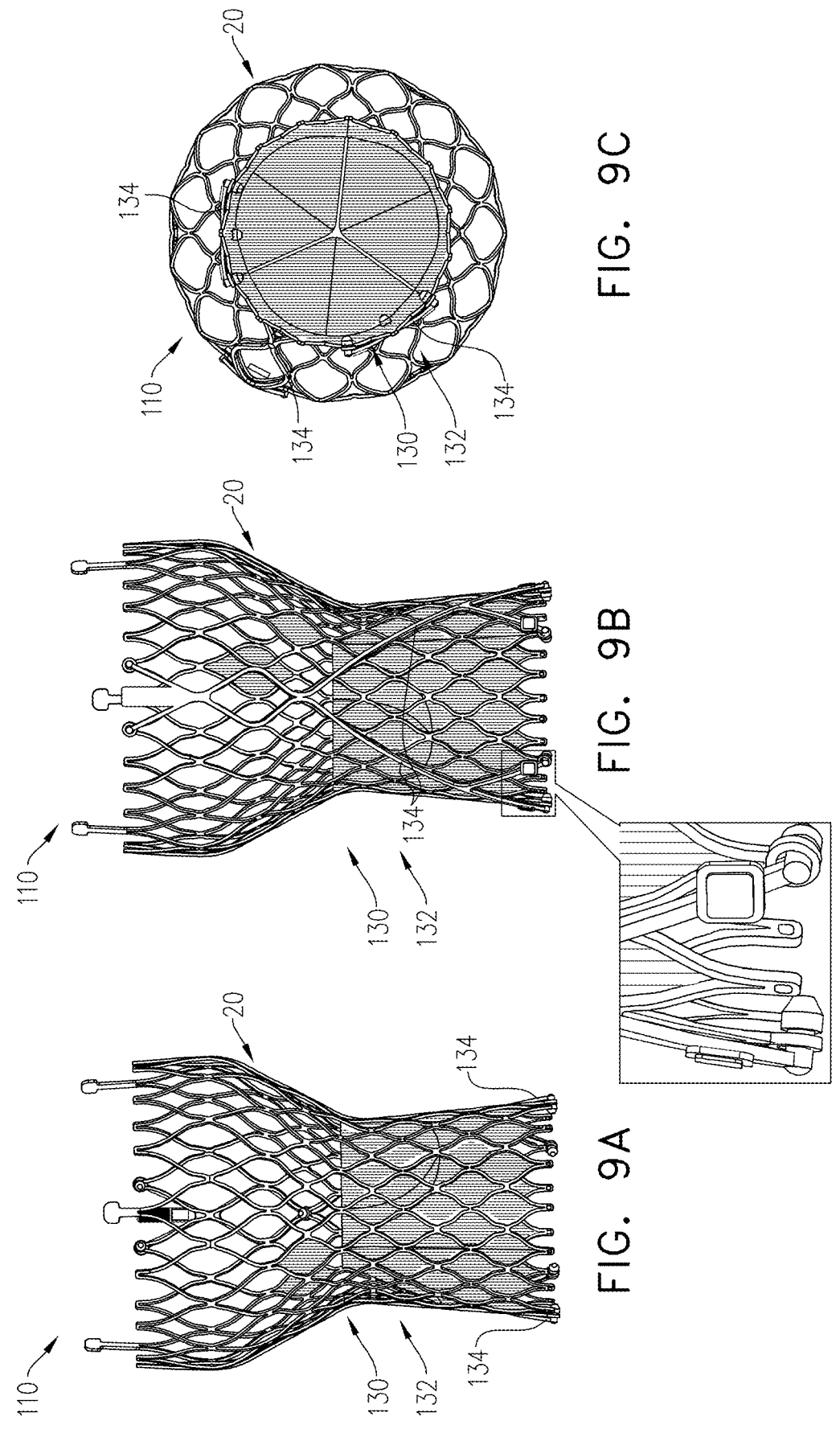
FIGS. 9A-C are schematic illustrations of several views of the prosthetic cardiac valve system of FIGS. 6 and 7 after attachment of the electrical-component add-on to a tubular frame of a prosthetic cardiac valve of the prosthetic cardiac valve system, in accordance with an application of the present invention.

Reference is still further made to FIGS. 9A-C, which are schematic illustrations of several views of prosthetic cardiac valve system 110 after attachment of electrical-component add-on 130 to tubular frame 22, in accordance with an application of the present invention.

Figure 10:
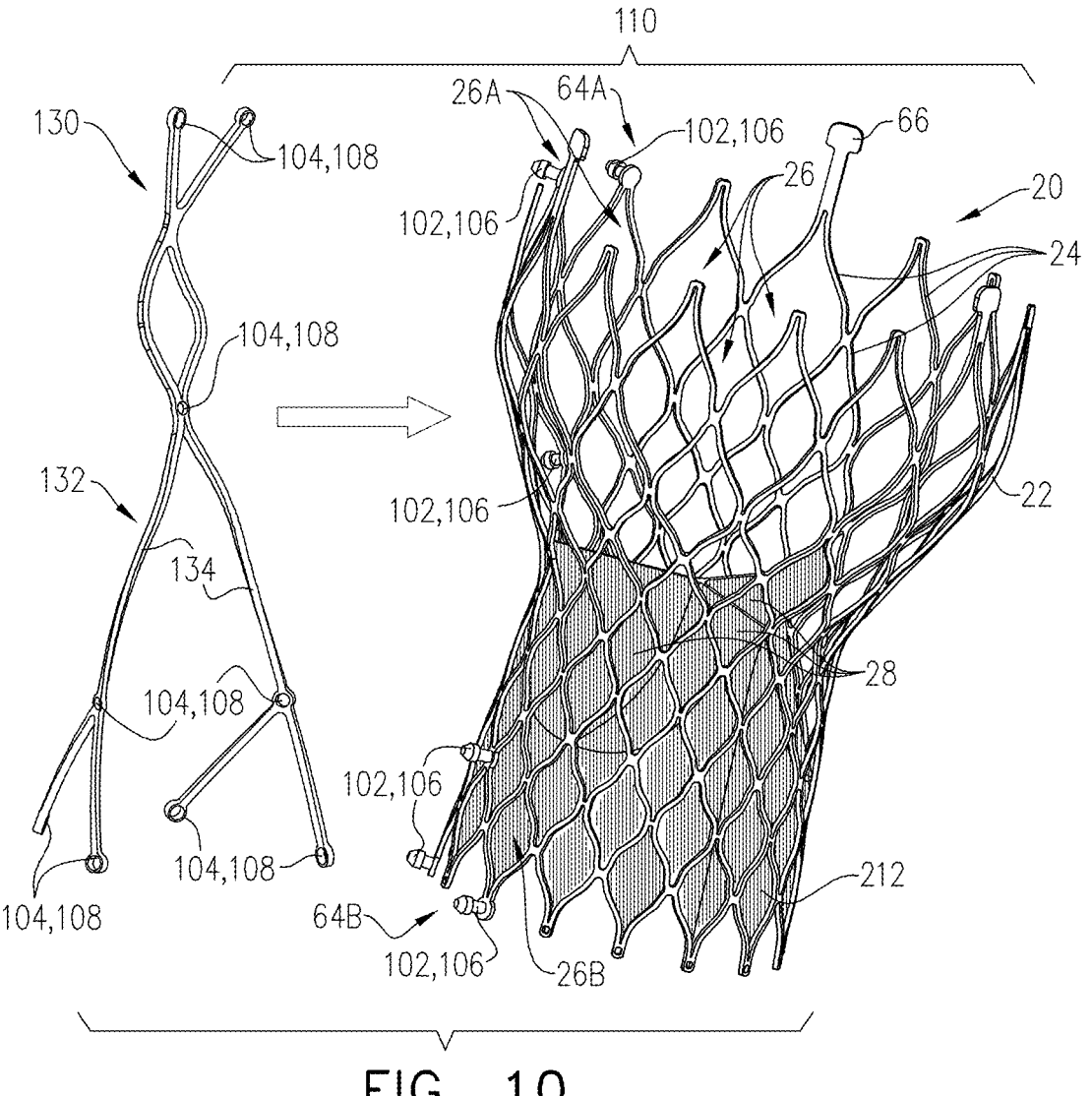
FIG. 10 is a schematic illustration of an alternative configuration of the prosthetic cardiac valve system of FIG. 6, in accordance with an application of the present invention.

Reference is still further made to FIG. 10, which is a schematic illustration of an alternative configuration of prosthetic cardiac valve system 110, in accordance with an application of the present invention.

Tubular frame 22 of prosthetic cardiac valve 20 of prosthetic cardiac valve system 110 defines respective snap-fastener first components 102. Electrical-component add-on 130 comprises:

a support 132, which is shaped so as to define snap-fastener second components 104, which are configured to snappingly engage snap-fastener first components 102, respectively, so as to attach support 132 to tubular frame 22 of prosthetic cardiac valve 20; and one or more electrical components 40, which are fixed to support 132.

The one or more electrical components 40 typically comprise one or more of the electrical components described hereinabove with reference to FIGS. 1-4C.

For some applications, support 132, when unconstrained, has a greatest dimension of at least 45 mm, no more than 65 mm, and/or 45-65 mm (for example, the greatest dimension may be a length, measured in a proximal-to-distal direction).

For some applications, support 132 is shaped so as to facilitate attachment of support 132 to a radially-outward surface of tubular frame 22, such as shown in FIGS. 6-10.

For some applications, support 132 is configured such that when support 132 is attached to tubular frame 22, support 132 surrounds less than 360 degrees of tubular frame 22, with respect to longitudinal axis 50 of tubular frame 22.

For some applications, support 132 is rotationally asymmetric when unconstrained, such as shown in FIGS. 6-10. When unconstrained, support 132 may be configured to have the shape shown in FIGS. 6 and 8A-D, or may be flatter, and only assume its final shape when attached to tubular frame 22, such as shown in FIGS. 7 and 9A-C.

For some applications, snap-fastener second components 104 are shaped so as to define respective studs 106, such as shown in FIGS. 6-10. For these applications, snap-fastener first components 102 are typically shaped as to define sockets 108 for snappingly receiving the studs 106, respectively. Sockets 108 may define respective through-holes or may be shaped so as to define respective receptacles having bottoms.

For other applications, snap-fastener second components 104 are shaped so as to define respective sockets 108, such as shown in FIG. 10. Sockets 108 may define respective through-holes or may be shaped so as to define respective receptacles having bottoms. For these applications, snap-fastener first components 102 are typically shaped as to define studs 106, for snapping insertion into sockets 108.

Reference is still made to FIGS. 6-10. For some applications, support 132 comprises support struts 134, which are shaped so as to define snap-fastener second components 104. For some applications, support struts 134 and stent struts 24 are shaped such that support struts 134 generally run along a portion of stent struts 24 when support 132 is attached to tubular frame 22.

For some of these applications, the one or more electrical components 40 further comprise one or more electrical leads 48. For some applications, the one or more electrical leads 48 are coated with an electrically insulating coating and coupled to at least a portion of support struts 134 (configuration not shown). For other applications, such as shown in FIGS. 8A-D and labeled in FIG. 8B, support struts 134 comprise electrical insulation, and a portion of support struts 134 electrically insulates the one or more electrical leads 48. For some of these applications, one or more of support struts 134 comprise an elongate portion of a flex PCB with which the one or more electrical leads 48 are integral (e.g., encased within the flex PCB, such as by lamination, or disposed on an external surface of the flex PCB and coated with an electrically insulating coating). For example, the flex PCB may comprise polyimide. Electrical leads 48 and the electrical insulation may implement any of the techniques described for leads and electrical insulation in the patents and patent applications incorporated herein by reference below, including, but not limited to above-mentioned International Appl. No. PCT/IL2024/050830, e.g., with reference to FIGS. 1A-B and/or 3A-H thereof.

For some applications, support struts 134 have:
a thickness of at least 50 microns, no more than 150 microns, and/or 50-150 microns,
a width of 300-1500 microns, and/or
a ratio of the width to the thickness of support struts 134 is 3-20.

Reference is still made to FIGS. 6-10. For some applications, the one or more electrical components 40 further comprise circuitry 46. For some of these applications, circuitry 46 comprises a PCB. For some applications, a single flex PCB is shaped so as to define (a) a circuitry portion to which the electronic components of circuitry 46 are coupled, and (b) an elongate portion, which defines one or more support struts 134, as described immediately above. Typically, the one or more electrical leads 48 electrically couple the one or more electrodes 44 to circuitry 46.

Reference is still made to FIGS. 6-10. For some applications, snap-fastener second components 104 are located on support 132 so as to facilitate attachment of support 132 to one or more proximal stent cells 26A at proximal end 64A of tubular frame 22, and to one or more distal stent cells 26B of tubular frame 22 at distal end 64B of tubular frame 22.

For some of these applications, snap-fastener second components 104 are located on support 132 so as to facilitate the attachment of support 132 to two or more distal stent cells 26B of tubular frame 22 at distal end 64B of tubular frame 22, such as to three or more, e.g., to four or more, distal stent cells 26B, and typically to no more than ten distal stent cells 26B. For some applications, snap-fastener second components 104 are located on support 132 so as to facilitate the attachment of support 132 to no more than 50% of the distal stent cells 26B of tubular frame 22.

For some applications, the two or more distal stent cells 26B include first 70 and second 72 distal stent cells 26B, which are separated from each other around tubular frame 22 by at least one intervening third 74 distal stent cell 26B. Snap-fastener second components 104 are located on support 132 so as to facilitate the attachment of support 132 to the first 70 and the second 72 distal stent cells 26B at distal end 64B of tubular frame 22 (and not necessarily to the intervening third 74 distal stent cell 26B).

For some applications, snap-fastener second components 104 are located on support 132 so as to facilitate the attachment of support 132 to two or more proximal stent cells 26A at proximal end 64A of tubular frame 22. Optionally, the two or more proximal stent cells 26A are adjacent to each other around tubular frame 22, such as shown.

For some applications, tubular frame 22 of prosthetic cardiac valve 20 is radially compressible, and is configured to elongate when radially compressed (i.e., crimped). Support struts 134 are configured to accommodate elongation of tubular frame 22 during radial compression and the elongation of tubular frame 22 while support 132 is attached to tubular frame 22. For example, support 132 may be elongatable, in at least one direction, by at least 2%, e.g., at least 3%, such as at least 4%, of an initial length of support 132, measured in the at least one direction while support 132 is unconstrained (for example, the greatest dimension may be a length, measured in a proximal-to-distal direction). The elongation may be facilitated by support 132 defining angles therealong, which straighten to allow elongation.

Reference is still made to FIGS. 6-10. For some applications, one or more of support struts 134 of support 132 are bifurcated to define two distal branches 136 and/or two proximal branches 138, as shown in FIGS. 6-10 and labeled in FIG. 8B. (If the support strut defines both two distal branches 136 and two proximal branches 138, such as shown, the support strut may be considered double-bifurcated.) Alternatively, one or more of support struts 134 may be divided into three or more distal branches and/or three or more proximal branches (configuration not shown). Optionally, one or more of electrical components 40 (e.g., antenna 42 and/or circuitry) are located between proximal branches 138, for example coupled to a junction between proximal branches 138 at the bifurcation.

The bifurcation may serve one or both of the following purposes:
the bifurcation may provide support for additional snap-fastener second components 104, i.e., respective snap-fastener second components 104 may be disposed on the branches, and/or
the bifurcation may provide support for additional electrodes 44, i.e., respective electrodes 44 may be disposed on the branches.
In the configuration shown in FIGS. 6-10, the bifurcation serves both purposes.

Figures 8A, 8B, 8C, 8D:
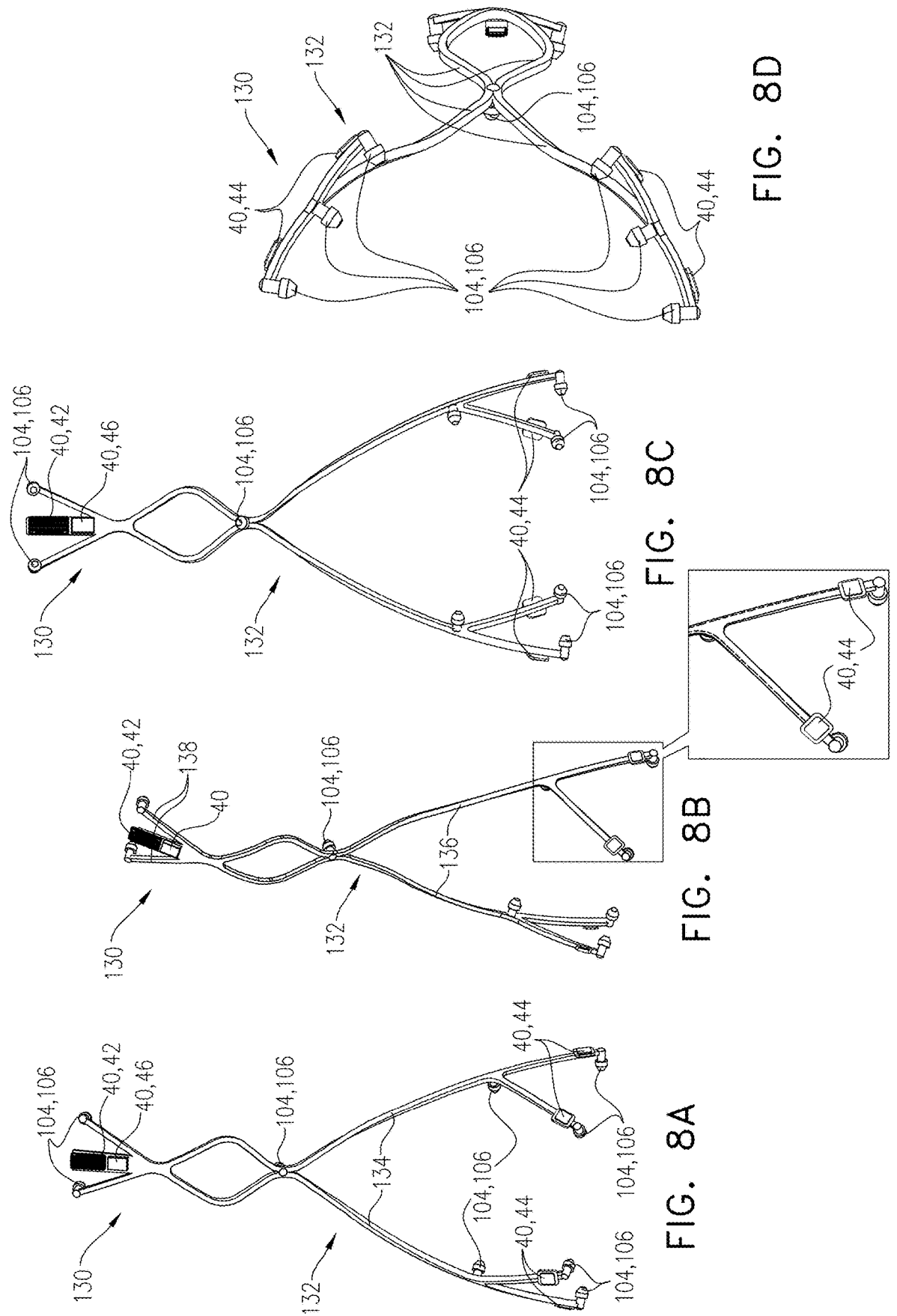
FIGS. 8A-D are schematic illustrations of several views of an electrical-component add-on of the prosthetic cardiac valve system of FIGS. 6 and 7, in accordance with an application of the present invention.

In some configurations in which the bifurcation provides support for additional electrodes 44, two separate electrical leads 48 are provided for the two electrodes 44, such as shown in FIG. 8B. In other configurations, the respective electrodes 44 of a given bifurcation may be electrically coupled together, in which case the electrode lead 48 of these electrodes may be bifurcated (configuration not shown, but shown in FIG. 3E of above-mentioned International Appl. No. PCT/IL2024/050830).

For some applications, electrical-component add-on 130 comprises two or more supports 132, which are shaped so as to define respective snap-fastener second components 104 and respective electrical components 40. Optionally, the electrical components of the supports 132 are electrically connected to one another.

Reference is made to FIGS. 1-10. In an application of the present invention, an electrical-component add-on is provided that is similar to electrical-component add-on 130, described hereinabove with reference to FIGS. 6-10, except that support 132, instead of defining snap-fastener second components 104, comprises one or more pockets 60, described hereinabove with reference to FIGS. 1-4C; in this configuration, support 132 typically does not comprise stretchable sheet 34, described hereinabove with reference to FIGS. 1-5.

Reference is again made to FIGS. 6-10. In some applications of the present invention, a method is provided that comprises bringing support 132 of electrical-component add-on 130 into contact with tubular frame 22 of prosthetic cardiac valve 20, and attaching support 132 to tubular frame 22 by snappingly engaging snap-fastener first components 102, defined by tubular frame 22, with snap-fastener second components 104 defined by support 132.

For some applications, the method is performed by a healthcare worker, e.g., a technician (as opposed to a manufacturing worker).

For some applications, the method further comprises, after attaching support 132 to tubular frame 22, radially compressing tubular frame 22 such that tubular frame 22 elongates. Support 132 struts are configured to accommodate elongation of tubular frame 22 during the radial compression and the elongation of tubular frame 22 while support 132 is attached to tubular frame 22.

Figures 11, 12:
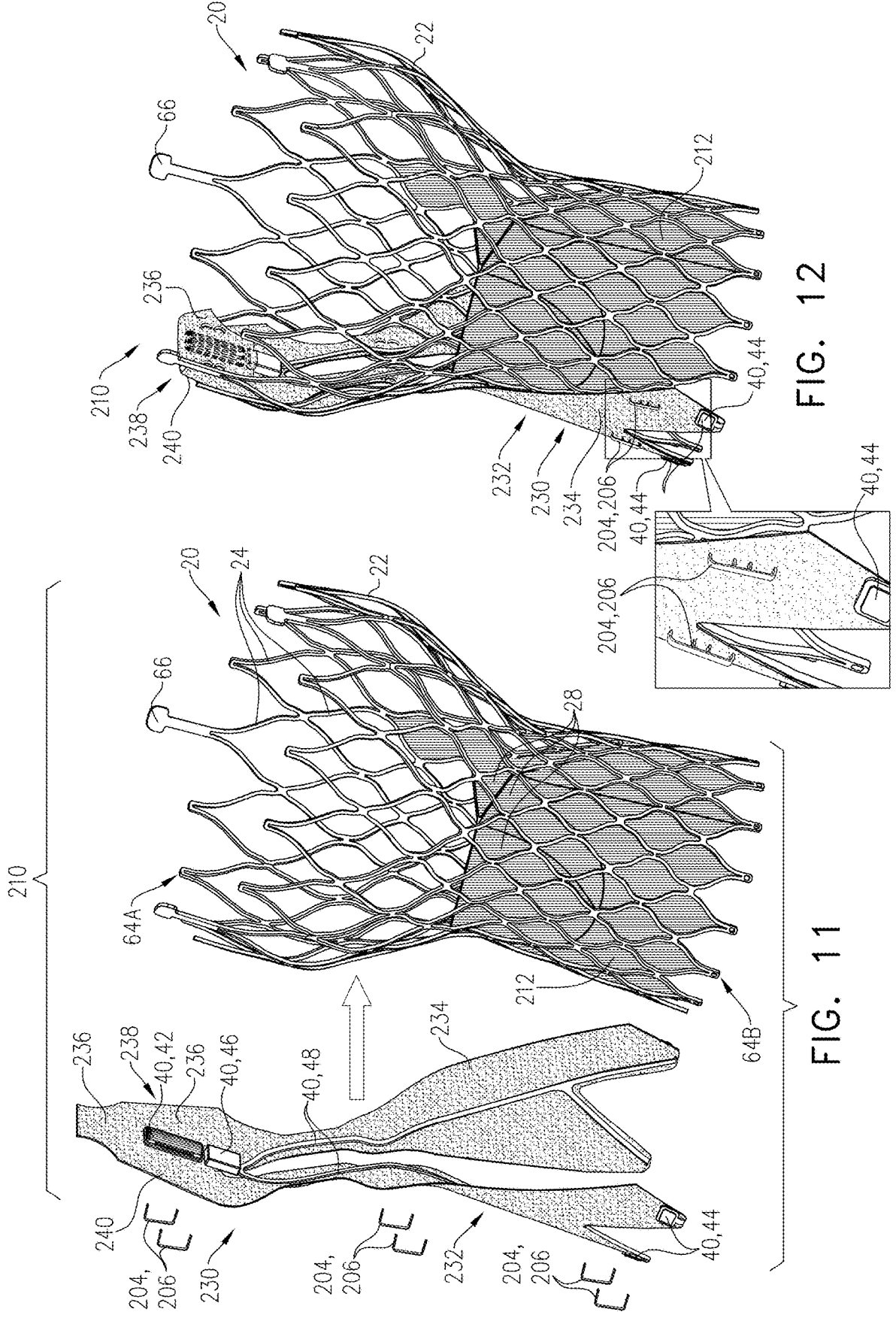
FIG. 11 is a schematic illustration of yet another prosthetic cardiac valve system, in accordance with an application of the present invention.
FIG. 12 is another schematic illustration of the prosthetic cardiac valve system of FIG. 11, in accordance with an application of the present invention.

Reference is now made to FIGS. 11 and 12, which are schematic illustrations of a prosthetic cardiac valve system 210, in accordance with an application of the present invention. Prosthetic cardiac valve system 210 comprises prosthetic cardiac valve 20 and an electrical-component add-on 230. Prosthetic cardiac valve system 210 may comprise additional elements, for example as described hereinbelow with reference to FIG. 13. Other than as described hereinbelow, prosthetic cardiac valve 20 may have any of the features thereof described hereinabove with reference to FIGS. 1-4C.

Electrical-component add-on 230 may optionally implement any of the features of electrical-component add-on 30, described hereinabove with reference to FIGS. 1-5, and/or electrical-component add-on 130, described hereinabove with reference to FIGS. 6-10. Prosthetic cardiac valve system 210 may implement any of the features of prosthetic cardiac valve system 10, described hereinabove with reference to FIGS. 1-5; and/or of prosthetic cardiac valve system 110, described hereinabove with reference to FIGS. 6-10, mutatis mutandis.

Electrical-component add-on 230 is configured to be easily attached to prosthetic cardiac valve 20, such as by a healthcare worker. FIG. 11 shows prosthetic cardiac valve system 210 prior to attachment of electrical-component add-on 230 to prosthetic cardiac valve 20, and FIG. 12 shows prosthetic cardiac valve system 210 after attachment of electrical-component add-on 230 to prosthetic cardiac valve 20. Typically, a healthcare worker attaches electrical-component add-on 230 to prosthetic cardiac valve 20 during or soon before an implantation procedure in which prosthetic cardiac valve 20 and attached electrical-component add-on 230 are implanted in a patient. For example, electrical-component add-on 230 may be attached to prosthetic cardiac valve 20 in an operating room or a cath lab.

Prosthetic cardiac valve system 210 further comprises a plurality of fasteners 204, which are configured to fasten electrical-component add-on 230 (typically a flexible sheet 234 thereof, if provided, such as described hereinbelow) to prosthetic cardiac valve 20. Typically, prosthetic cardiac valve system 210 comprises two-ten fasteners 204. Typically, fasteners 204 are configured to fasten by undergoing plastic deformation. For example, fasteners 204 may comprise:

staples 206, such as shown, each of which comprise a wire, both end of which are driven through two layers of material and clinched to hold the staple to the two layers of material, or rivets, each of which comprises a shell and a headed stem (mandrel); drawing the stem through the shell causes the shell to deform and clamp two layers of material together (configuration not shown).

As described above, prosthetic cardiac valve 20 comprises tubular frame 22 and a plurality of prosthetic leaflets 28. For some applications, prosthetic cardiac valve 20 further comprises a skirt 212, which comprises flexible sheeting, and covers a portion of tubular frame 22, typically distal to (upstream of) prosthetic leaflets 28. Skirt 212 may help prevent paravalvular leak (PVL). Skirt 212 may be attached to an inner surface of tubular frame 22 and/or to an external surface of tubular frame 22. For example, skirt 212 may comprise polyethylene terephthalate (PET), polyurethane (PU), or pericardium, such as bovine or porcine pericardium.

For some applications, electrical-component add-on 230 comprises a support 232, comprising flexible sheet 234; and one or more electrical components 40, which are fixed to support 232. The one or more electrical components 40 typically comprise one or more of the electrical components described hereinabove with reference to FIGS. 1-4C.

For some applications, support 232 is shaped so as to facilitate attachment of support 232 to a radially-outward surface of prosthetic cardiac valve 20, such as shown in FIGS. 11-12.

For some applications, support 232 is configured such that when support 232 is attached to prosthetic cardiac valve 20, support 232 surrounds less than 360 degrees of prosthetic cardiac valve 20, with respect to longitudinal axis 50 of tubular frame 22.

For some applications, support 232 is rotationally asymmetric when unconstrained, such as shown in FIGS. 11-12. When unconstrained, support 232 may be configured to have the shape shown in FIG. 11, or may be flatter, and only assume its final shape when attached to prosthetic cardiac valve 20, such as shown in FIG. 12.

For some applications, flexible sheet 234 is stretchable (typically elastic), such as in order to accommodate elongation of tubular frame 22 during radial compression and the elongation of tubular frame 22 while support 232 is attached to tubular frame 22.

For some applications, at least a portion of fasteners 204 are configured to fasten electrical-component add-on 230 (typically flexible sheet 234 thereof, if provided) to skirt 212 of prosthetic cardiac valve 20. For some of these applications, the at least a portion of fasteners 204 are configured to fasten flexible sheet 234 of electrical-component add-on 230 to skirt 212.

Reference is still made to FIG. 11-12. For some applications, flexible sheet 234 is shaped so as to define a flap 236, e.g., at a proximal end portion 238 of flexible sheet 234. Flap 236 is configured to be folded over a portion of stent struts 24 of tubular frame 22, such that flap 236 is disposed radially inside tubular frame 22 alongside a portion 240 of flexible sheet 234 disposed radially outside tubular frame 22. A portion of fasteners 204 are configured to attach electrical-component add-on 230 to prosthetic cardiac valve 20 by fastening portion 240 of flexible sheet 234 to flap 236, thereby sandwiching some of stent struts 24 between flap 236 and portion 240 of flexible sheet 234. Providing flap 236 at proximal end portion 238 of flexible sheet 234 may facilitate attachment of a proximal portion of electrical-component add-on 230 to a proximal portion of prosthetic cardiac valve 20 that lacks skirt 212, and thus lacks a suitable sheet to which fasteners 204 may be readily fastened. In addition, the covering of antenna 42 and/or other circuitry by flap 236 may aid with endothelialization of the antenna and/or other circuitry.

For other applications (configuration not shown), flexible sheet 234, instead of begin shaped so as to define flap 236, flexible sheet 234 is shaped so as to define a pocket 60 at proximal end portion 238 of flexible sheet 234. Pocket 60 is shaped so as to receive one or more proximal stent cells 26A, so as to facilitate the attachment of support 232 to the one or more proximal stent cells 26A at proximal end 64A of tubular frame 22. Fasteners 204 may or may not be used to secure the walls of pocket 60 to each other after the one or more proximal stent cells 26A have been inserted into pocket 60. Pocket 60 may implement any of the features described hereinabove with reference to FIGS. 1-4C, mutatis mutandis.

For some applications, flexible sheet 234, when unconstrained in a non-stretched state, has:

a surface area of at least 720 mm2, no more than 1000 mm2, and/or 720-1000 mm2, and/or a greatest dimension of at least 45 mm, no more than 65 mm, and/or 45-65 mm (for example, the greatest dimension may be a length, measured in a proximal-to-distal direction) (for applications in which flap 236 is configured to be folded, the greatest dimension is measured before folding).

For some applications, electrical-component add-on 230 comprises two or more supports 232, which comprise respective flexible sheets 234 and respective electrical components 40. Optionally, the electrical components of the supports 232 are electrically connected to one another.

Reference is still made to FIG. 11-12. In some applications of the present invention, a method is provided that comprises bringing support 232 of electrical-component add-on 230 into contact with prosthetic cardiac valve 20, and fastening flexible sheet 234 of electrical-component add-on 230 to prosthetic cardiac valve 20 using the plurality of fasteners 204.

For some applications, the method is performed by a healthcare worker, e.g., a technician (as opposed to a manufacturing worker).

For some applications, fasteners 204 comprise staples 206, and fastening flexible sheet 234 of electrical-component add-on 230 to prosthetic cardiac valve 20 comprises stapling flexible sheet 234 of electrical-component add-on 230 to prosthetic cardiac valve 20.

For some applications, fastening electrical-component add-on 230 to prosthetic cardiac valve 20 comprises using at least a portion of fasteners 204 to fasten flexible sheet 234 of electrical-component add-on 230 to skirt 212 of prosthetic cardiac valve 20.

For some applications in which flexible sheet 234 is shaped so as to define flap 236, fastening electrical-component add-on 230 to prosthetic cardiac valve 20 comprises:

folding flap 236 over a portion of stent struts 24 of tubular frame 22, such that flap 236 is disposed radially inside tubular frame 22 alongside portion 240 of flexible sheet 234 disposed radially outside tubular frame 22; and using a portion of fasteners 204 to attach electrical-component add-on 230 to prosthetic cardiac valve 20 by fastening portion 240 of flexible sheet 234 to flap 236.

For some applications in which flexible sheet 234 is stretchable, the method further comprises, after attaching support 232 to prosthetic cardiac valve 20, radially compressing tubular frame 22 such that tubular frame 22 elongates. Stretchable flexible sheet 234 is configured to accommodate elongation of tubular frame 22 during the radial compression and the elongation of tubular frame 22 while support 232 is attached to tubular frame 22.

Figure 13:
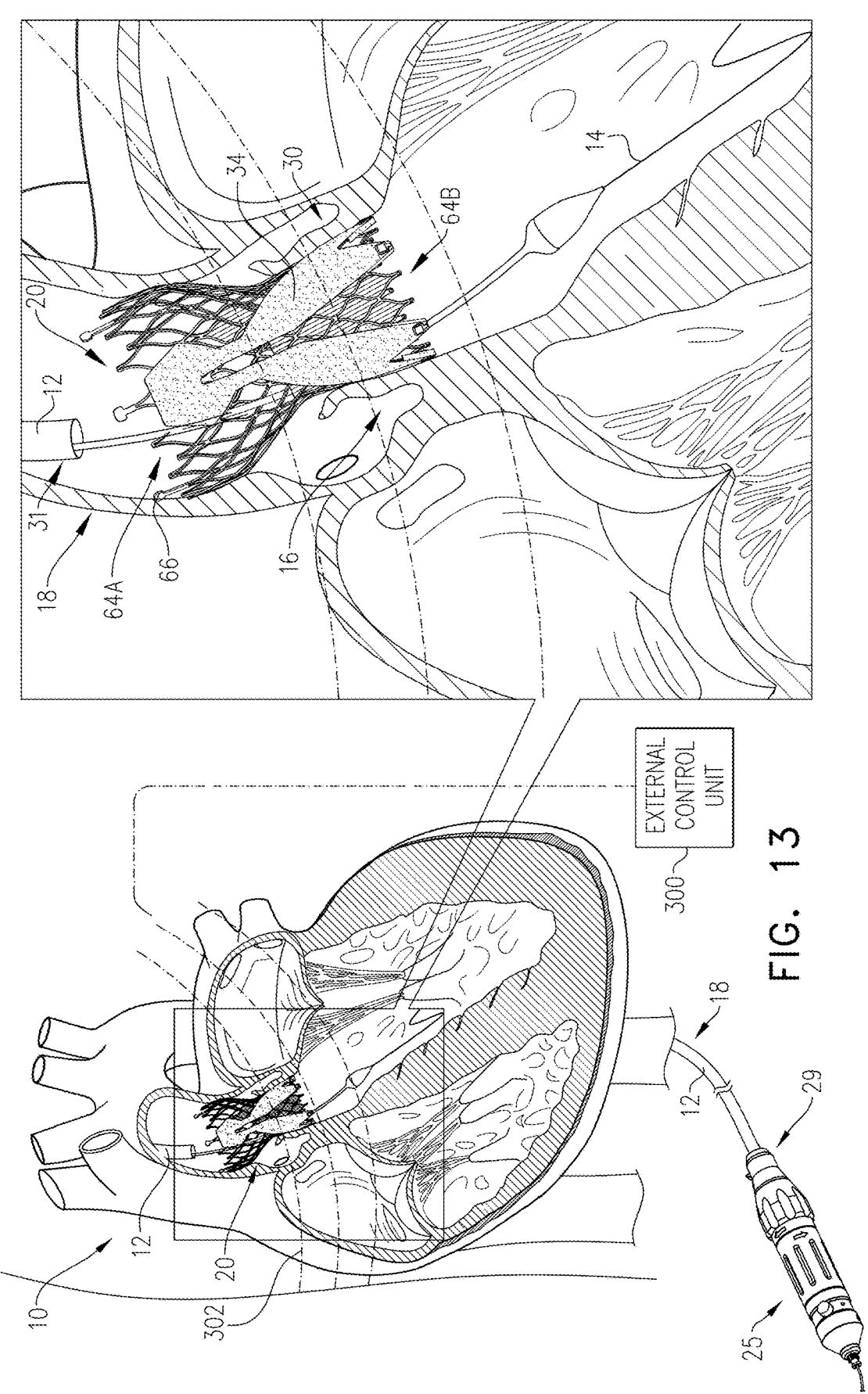
FIG. 13 is a schematic illustration of one configuration of the prosthetic cardiac valve system of FIGS. 1 and 2 and a prosthetic cardiac valve thereof implanted in a body of a patient, in accordance with an application of the present invention.

Reference is now made to FIG. 13, which is a schematic illustration of one configuration of prosthetic cardiac valve system 10 and prosthetic cardiac valve 20 implanted in the body of the patient, in accordance with an application of the present invention. By way of example and not limitation, FIG. 13 shows prosthetic cardiac valve system 10 (comprising electrical-component add-on 30). Prosthetic cardiac valve system 110, described hereinabove with reference to FIGS. 6-10, and prosthetic cardiac valve system 210, described hereinabove with reference to FIGS. 11-12, may be deployed and used in the same manner. Also by way of example and not limitation, prosthetic cardiac valve 20 is shown in FIG. 13 as comprising a prosthetic aortic valve.

Prosthetic cardiac valve system 10 further comprises a delivery system 18, which typically comprises a delivery sheath 12 and is used with a guidewire 14. Delivery system 18 typically further comprises a user-control handle 25, which is disposed at (and optionally coupled to) a proximal end portion 29 of delivery sheath 12. The opposite, free end portion of delivery sheath 12 is thus a distal end portion 31 of delivery sheath 12. Prosthetic cardiac valve 20 is typically configured to be delivered to a native cardiac valve 16 of the patient (e.g., a native aortic valve, as shown in FIG. 13) in a constrained delivery configuration within delivery sheath 12. Distal end portion 31 of delivery sheath 12 may be a conventional tube, for example as shown. Alternatively, distal end portion 31 of delivery sheath 12 may further comprise a capsule that is moveable distally with respect to the remainder of delivery sheath 12 during deployment. All or a portion of prosthetic cardiac valve 20 may be contained within the capsule. As used in the present application, including in the claims and Inventive Concepts, in configurations in which distal end portion 31 comprises a capsule (or other type of holder), the distal end portion 31 of delivery sheath 12 refers to the combination of the conventional tubular portion of the sheath and the capsule. By way of example and not limitation, such a capsule is described in U.S. Pat. No. 10,888,421 to Hariton et al., which is incorporated herein by reference.

Typically, prosthetic cardiac valve 20 is deployed using imaging, such as fluoroscopy, and is rotated if necessary during the deployment to position the electrodes 44 at desired rotational locations.

Reference is still made to FIG. 13. Typically, an external system is provided that is configured to be disposed outside the body of the patient. The external system comprises an external control unit 300.

For some applications, the external system further comprises an external transmitter and/or receiver, which optionally comprises an external coil 302, which is highly schematically illustrated in FIG. 13. For example, external coil 302 may be configured to be placed around the subject's chest, such as schematically shown in FIG. 13, or placed against the chest without surrounding the chest, such as against the sternum (configuration not shown). The external transmitter and/or receiver is configured to wirelessly transfer energy to at least one of the one or more prosthetic-valve coils of antenna 42, such as by driving external coil 302 to wirelessly transfer the energy to at least one of the one or more prosthetic-valve coils by inductive coupling. For example, the external transmitter may transmit RF energy at a frequency of 2-300 MHz, e.g., 6.78 MHz.

For some applications in which the one or more electrical components 40 comprise circuitry 46 and the one or more electrode 44, the circuitry is configured to apply pacing to the heart using the one or more electrodes 44. For example, in configurations in which prosthetic cardiac valve 20 comprises a prosthetic aortic valve, the pacing may be applied temporarily for up to several weeks after implantation of the prosthetic aortic valve, typically using an external control unit to continuously provide power, such as described hereinabove, or applied longer-term, in which case the prosthetic aortic valve may further comprise an energy storage module, e.g., comprising a battery, which may be periodically charged using the external control unit. Further alternatively or additionally, for some applications, the circuitry is configured to apply rapid pacing during an invasive structural heart procedure, such as an implantation procedure, such as a transcatheter aortic valve replacement (TAVR) procedure, or a TAVR-in-TAVR procedure in which the first TAVR comprises the prosthetic aortic valve.

For some applications, circuitry 46 is configured to apply a pacing signal using all of electrodes 44. For other applications, circuitry 46 is configured to apply the pacing signal using fewer than all of electrodes 44, e.g., (a) fewer than all of the cathodes, for example, using just a single one of the cathodes, or two or more cathodes of three or more provided cathodes, and/or fewer than all of the anodes, for example, using just a single one of the anodes, or two or more anodes of three or more provided anodes.

Optionally, in configurations in which the electrical-component add-on comprises a plurality of distal (e.g., upstream) electrodes 44, one or more of the distal electrodes 44 are activated as one or more anodes, and one or more other distal (e.g., upstream) electrodes 44 are activated as one or more cathodes; in other words, any given distal electrode 44 can be activated as either an anode or a cathode.

In general, any of electrodes 44 (regardless of their location on tubular frame 22) can be configured as an anode or a cathode.

For some applications, circuitry 46 separately activates each of electrodes 44, e.g., cathodes and/or anodes, at different times in different combinations, and, based on a determination of which of the electrodes 44 (e.g., the cathodes, and/or the anodes in configurations in which a plurality of anodes are provided) provides the most effective pacing, i.e., the pacing that is successfully obtained using the smallest stimulation voltage. Circuitry 46 uses this most effective combination of electrodes 44, e.g., cathode(s) or anode(s), for future pacing.

For some applications, the determination regarding the most effective pacing is made based on the sensed ECG, based on the combination of electrodes that results in the lowest ECG sensing threshold. Alternatively or additionally, for some applications, the determination regarding the most effective pacing is made by selecting the combination of electrodes that yields the lowest power, voltage, or current threshold sufficient for pacing, i.e., successful generation of a cardiac action potential.

In general, circuitry 46 is configured to apply the weakest pacing signal that yields an action potential in the heart. Circuitry 46 may be configured to induce pacing at a set voltage level or alternatively may be set to automatically determine the minimal voltage level of stimulation for a sufficient pacing.

For example, this determination regarding the most effective pacing may be made by circuitry 46 and/or by circuitry of an external control unit, such as external control unit 300, described hereinabove with reference to FIG. 13. For some applications, this determination is performed (a) only once at the setup of the device immediately after implantation, (b) periodically, e.g., approximately once per day or once per week, and/or (c) before each pacing pulse is applied. An operator may or may not be involved in making the determination.

Figures 14, 15:
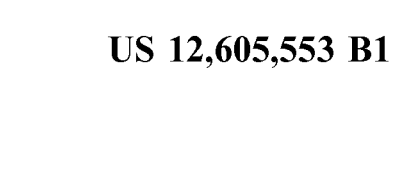
FIG. 14 is a schematic illustration of yet another a prosthetic cardiac valve system, in accordance with an application of the present invention.
FIG. 15 is a schematic illustration of the prosthetic cardiac valve system of FIG. 14, in accordance with an application of the present invention.

Reference is now made to FIGS. 14 and 15, which are schematic illustrations of a prosthetic cardiac valve system 310, in accordance with an application of the present invention. Prosthetic cardiac valve system 310 comprises prosthetic cardiac valve 20 and an electrical-component add-on 330. Prosthetic cardiac valve system 310 may comprise additional elements, for example as described hereinabove with reference to FIG. 13 and/or hereinbelow with reference to FIGS. 22A-E. Electrical-component add-on 330 may optionally implement any of the features of electrical-component add-on 30, described hereinabove with reference to FIGS. 1-5; electrical-component add-on 130, described hereinabove with reference to FIGS. 6-10; and/or electrical-component add-on 230, described hereinabove with reference to FIGS. 11-12. Other than as described hereinbelow, prosthetic cardiac valve 20 may have any of the features thereof described hereinabove with reference to FIGS. 1-4C. Prosthetic cardiac valve system 310 may implement any of the features of prosthetic cardiac valve system 10, described hereinabove with reference to FIGS. 1-5; of prosthetic cardiac valve system 110, described hereinabove with reference to FIGS. 6-10; and/or of prosthetic cardiac valve system 210, described hereinabove with reference to FIGS. 11-12, mutatis mutandis.

Electrical-component add-on 330 is configured to be easily attached to tubular frame 22 of prosthetic cardiac valve 20 within the patient's body by a surgeon during an implantation procedure. FIG. 14 shows prosthetic cardiac valve system 310 prior to attachment of electrical-component add-on 330 to tubular frame 22, and FIG. 15 shows prosthetic cardiac valve system 310 after attachment of electrical-component add-on 330 to tubular frame 22 (for clarity of illustration, anatomy is not shown).

Figure 16B:
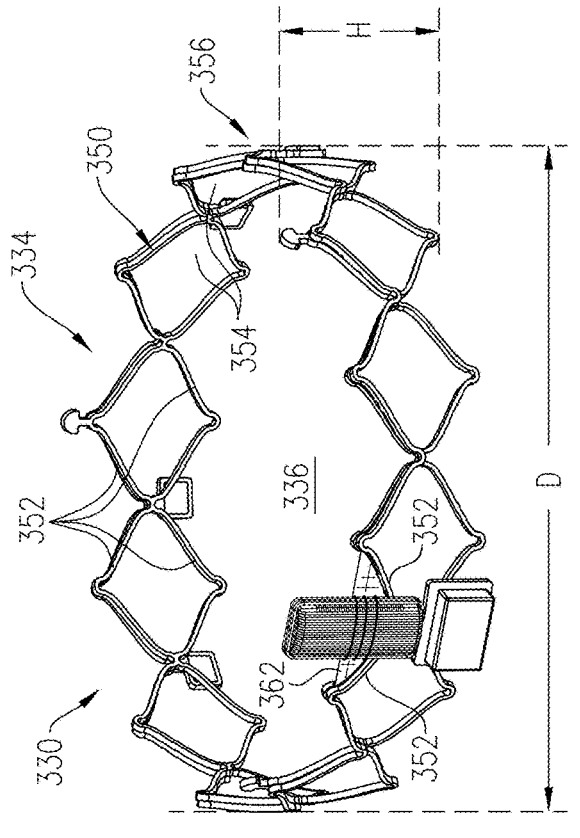
FIGS. 16A-C are schematic illustrations of several views of an electrical-component add-on of the prosthetic cardiac valve system of FIGS. 14 and 15 in a deployed configuration, in accordance with an application of the present invention.
Figure 16A:
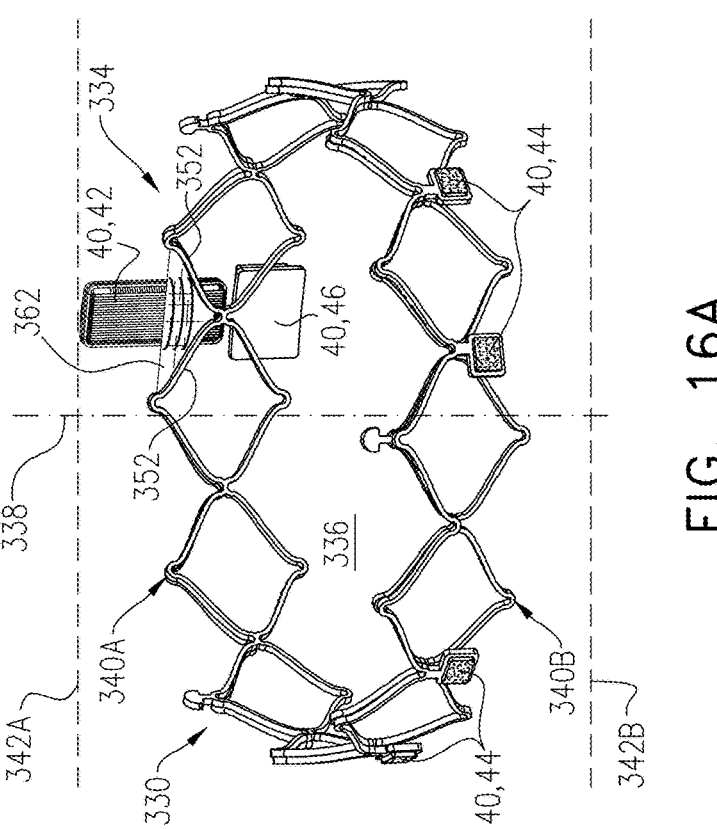
Figure 16C:
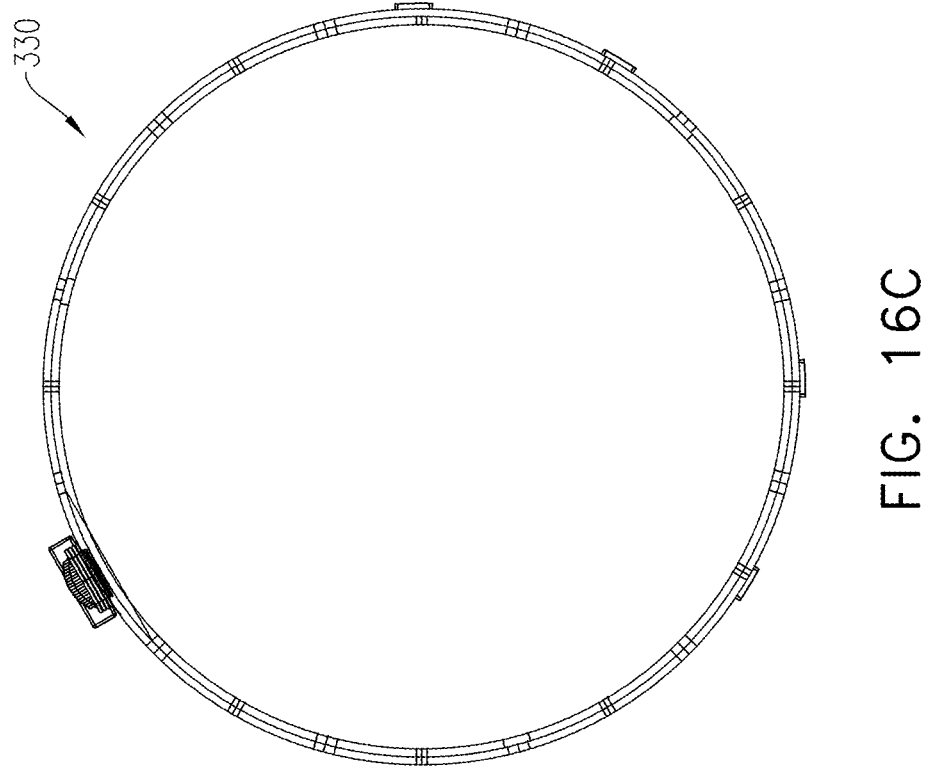

Reference is still made to FIGS. 14 and 15, and is further made to FIGS. 16A-C, which are schematic illustrations of several views of electrical-component add-on 330 in a deployed configuration, in accordance with an application of the present invention. Typically, the deployed configuration is a radially-expanded deployed configuration.

Figure 17:
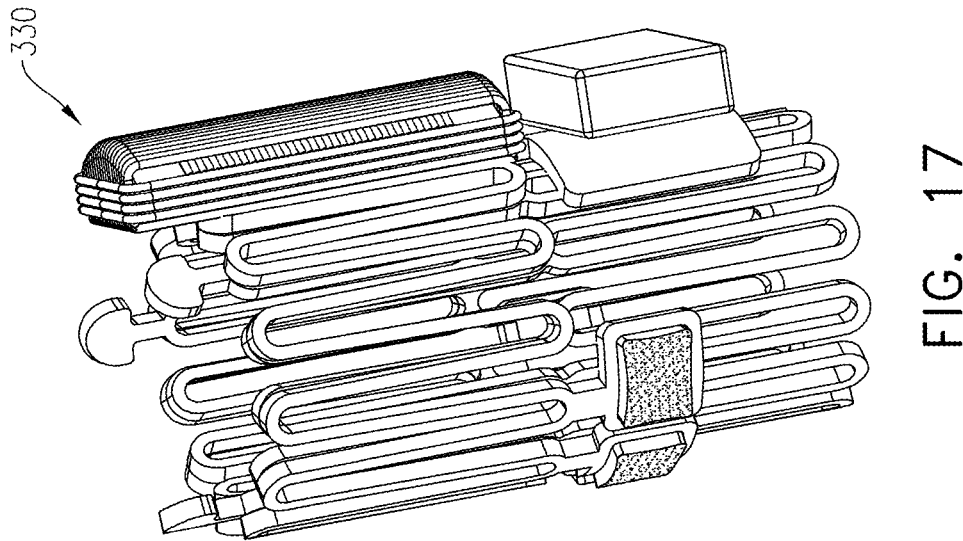
FIG. 17 is a schematic illustration of the electrical-component add-on of FIGS. 16A-C in a delivery configuration, in accordance with an application of the present invention.

Reference is still further made to FIG. 17, which is a schematic illustration of electrical-component add-on 330 in a delivery configuration, in accordance with an application of the present invention. Typically, the delivery configuration is a radially-compressed compressed delivery configuration. For clarity of illustration, a delivery sheath is not shown, even though electrical-component add-on 330 is typically disposed within a delivery sheath when in the radially-compressed delivery configuration, such as described hereinbelow with reference to FIG. 22A.

In some applications of the present invention, electrical-component add-on 330 comprises:

a support 332; and one or more electrical components 40, which are supported by support 332.

Support 332 is configured to assume a delivery configuration, such as shown in FIG. 17, and a deployed configuration, such as shown in FIGS. 14, 15, and 16A-C. Support 332 is configured to be positioned above, at, or below an annulus of a native cardiac valve of a heart, such as described hereinbelow with reference to FIG. 22B. Support 332 is shaped as a ring 334 when in the deployed configuration, such as shown in FIGS. 14 and 16A-C, so as to receive tubular frame 22 of prosthetic cardiac valve 20 within support 332, such as shown in FIG. 15.

The one or more electrical components 40 may comprise any of the electrical components described hereinabove for electrical-component add-on 30, with reference to FIGS. 1, 2, 3A-D, and 4A-C.

For some applications, antenna 42 comprises at least one prosthetic-valve coil that is not coaxial with support 332 when support 332 is in the deployed configuration, such as shown in FIGS. 14, 15, and 16A-C.

Typically, electrical-component add-on 330 does not comprise valve leaflets.

Support 332 is shaped so as to surround a lumen 336 (labeled in FIGS. 16A-B) when in the deployed configuration. Optionally, lumen 336 is free of the one or more electrical components 40.

As labeled in FIG. 16A, when support 332 is in the deployed configuration, support 332 defines a central longitudinal axis 338 and has a proximal end 340A and a distal end 340B. For some applications, when support 332 is in the deployed configuration, the one or more electrodes 44 are disposed axially between an axial location 342A proximal to proximal end 340A (e.g., 10 mm, such as 5 mm, proximal to proximal end 340A) and an axial location 342B distal to distal end 340B (e.g., 10 mm, such as 5 mm, distal to distal end 340B). For some of these applications, when support 332 is in the deployed configuration, the one or more electrodes 44 are disposed axially between proximal end 340A and distal end 340B of support 332, such as shown.

For some applications, when support 332 is in the deployed configuration, the one or more electrical components 40 are disposed axially between axial location 342A and axial location 342B, such as shown.

For some applications, support 332 is configured such that radial expansion of tubular frame 22 within support 332 radially expands support 332 and anchors support 332 in place above, at, or below the annulus, such as described hereinbelow with reference to FIG. 22D.

Optionally, support 332 comprises barbs or other anchoring elements for anchoring, or assisting with anchoring, support 332 to cardiac tissue above, at, or below the annulus (configuration not shown). Alternatively, support 332 does not comprise anchoring elements, such as shown.

Optionally, support 332 comprises barbs or other coupling elements for coupling support 332 to tubular frame 22 and/or other elements of prosthetic cardiac valve 20, such as skirt 212 (configuration not shown). Alternatively, support 332 does not comprise coupling elements, such as shown.

For some applications, such as labeled in FIG. 16B, support 332, when in the deployed configuration, has:
a height H of at least 5 mm (e.g., at least 7 mm), no more than 15 mm (e.g., no more than 10 mm), and/or 5-15 mm, such as 7-10 mm, and/or
an outer diameter D of at least 19 mm, no more than 35 mm, and/or 19-35 mm.
For some applications, as labeled in FIG. 16B, support 332 comprises a tubular stent 350 comprising interconnected stent struts 352. Optionally, interconnected stent struts 352 are arranged so as to define interconnected stent cells 354.

For some of these applications, interconnected stent struts 352 are arranged so as to define exactly one row 356 (as shown) or exactly two rows 356 (configuration not shown) of interconnected stent cells 354. For some applications, interconnected stent struts 352 are arranged so as to define 5-18 interconnected stent cells 354 per row. Tubular stent 350 may be self-expandable, e.g., comprising a shape-memory alloy, or may be balloon-expandable, both as generally known in the stent art. Optionally, stent struts 352 are radiopaque and/or support 332 comprises one or more radiopaque markers attached to tubular stent 350.

For some of these applications, support 332 further comprises a flexible sheet 362, which is mechanically coupled to two or more of interconnected stent struts 352, such as by stitching, such as shown, or using alternative coupling techniques that are known in the art. Flexible sheet 362 may comprise, for example, a polymer (e.g., polyethylene terephthalate (PET) or expanded Polytetrafluoroethylene (ePTFE)) or biological tissue, e.g., a pericardium sheet. Optionally, the material of flexible sheet 362 is woven. Optionally, the material of flexible sheet 362 comprises cloth. Flexible sheet 362 is collapsible with support 332 when support 332 assumes the delivery configuration.

In these applications, at least one of the one or more electrical components 40, such as antenna 42, is mechanically coupled to tubular stent 350 at least in part by being mechanically coupled to flexible sheet 362. The at least one of the one or more electrical components 40 is mechanically coupled to flexible sheet 362 by stitching, such as shown, or using alternative coupling techniques that are known in the art.

Figures 18, 19:
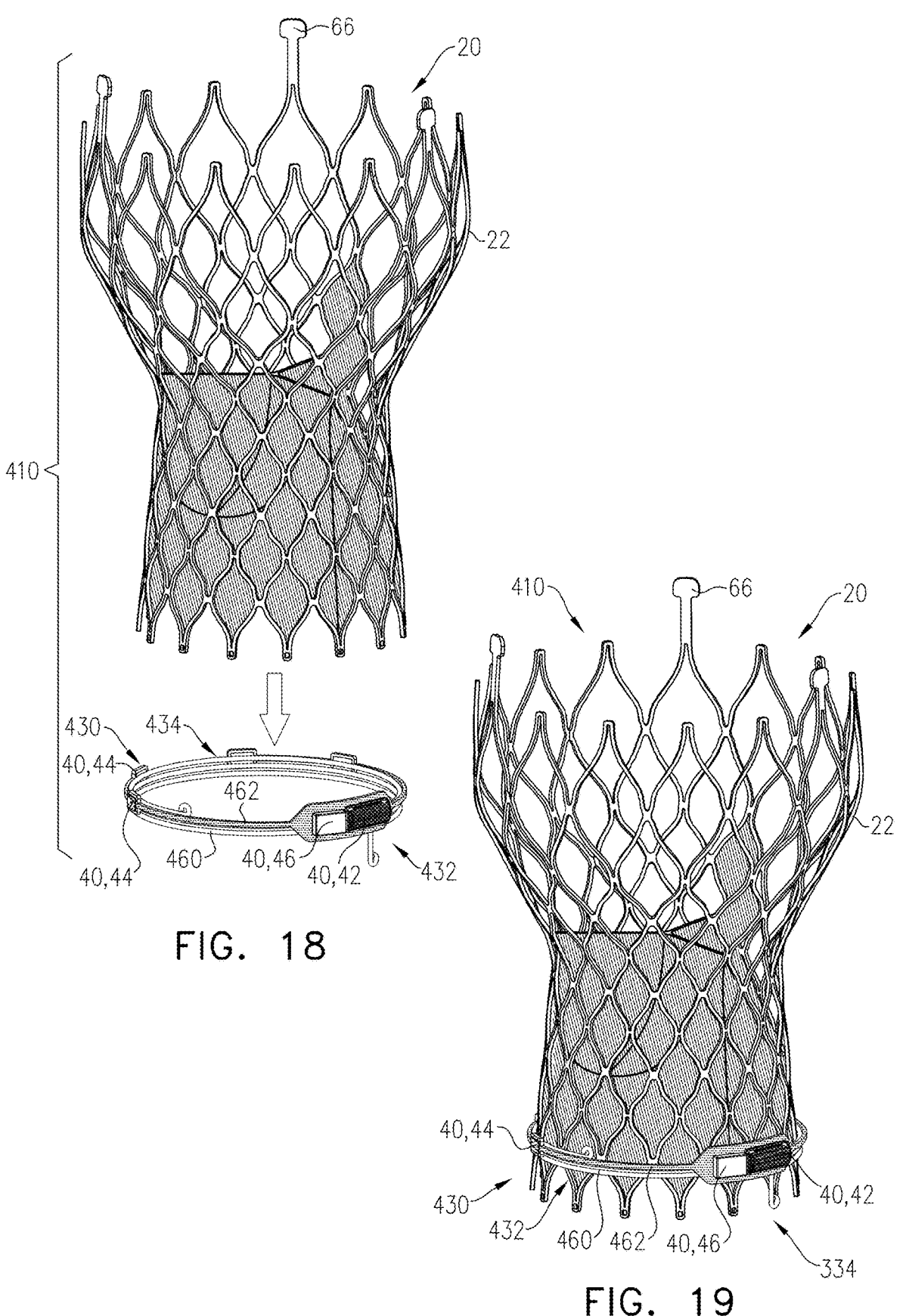
FIG. 18 is a schematic illustration of still another a prosthetic cardiac valve system, in accordance with an application of the present invention.
FIG. 19 is a schematic illustration of the prosthetic cardiac valve system of FIG. 18, in accordance with an application of the present invention.

Reference is now made to FIGS. 18 and 19, which are schematic illustrations of a prosthetic cardiac valve system 410, in accordance with an application of the present invention. Prosthetic cardiac valve system 410 comprises prosthetic cardiac valve 20 and an electrical-component add-on 430. Prosthetic cardiac valve system 410 may comprise additional elements, for example as described hereinabove with reference to FIG. 13 and/or hereinbelow with reference to FIGS. 23A-E. Other than as described below, electrical-component add-on 430 is similar to electrical-component add-on 330, described hereinabove with reference to FIGS. 14-17, and may implement any of the features thereof, mutatis mutandis, and have any of the characteristics, including dimensions thereof. In addition, electrical-component add-on 430 may optionally implement any of the features of electrical-component add-on 30, described hereinabove with reference to FIGS. 1-5; electrical-component add-on 130, described hereinabove with reference to FIGS. 6-10; and/or electrical-component add-on 230, described hereinabove with reference to FIGS. 11-12. Other than as described hereinbelow, prosthetic cardiac valve 20 may have any of the features thereof described hereinabove with reference to FIGS. 1-4C. Prosthetic cardiac valve system 410 may implement any of the features of prosthetic cardiac valve system 10, described hereinabove with reference to FIGS. 1-5; of prosthetic cardiac valve system 110, described hereinabove with reference to FIGS. 6-10; of prosthetic cardiac valve system 210, described hereinabove with reference to FIGS. 11-12; and/or of prosthetic cardiac valve system 310, described hereinabove with reference to FIGS. 14-17, mutatis mutandis.

Electrical-component add-on 430 is configured to be easily attached to tubular frame 22 of prosthetic cardiac valve 20 within the patient's body by a surgeon during an implantation procedure. FIG. 18 shows prosthetic cardiac valve system 410 prior to attachment of electrical-component add-on 430 to tubular frame 22, and FIG. 19 shows prosthetic cardiac valve system 410 after attachment of electrical-component add-on 430 to tubular frame 22 (for clarity of illustration, anatomy is not shown).

Reference is still made to FIGS. 18 and 19, and is further made to FIGS. 20A-C, which are schematic illustrations of several views of electrical-component add-on 430 in a deployed configuration, in accordance with an application of the present invention.

Figure 21:
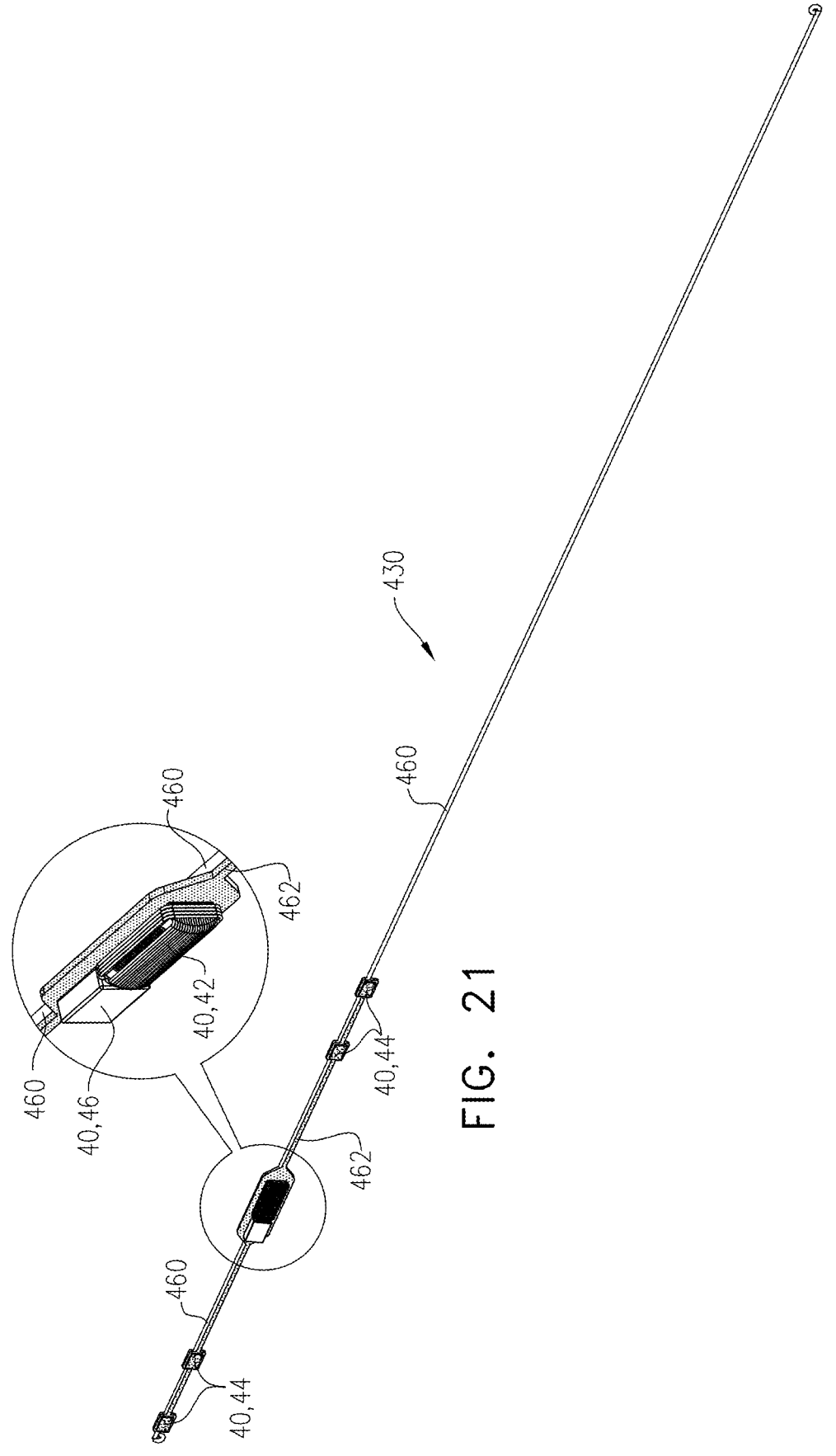
FIG. 21 is a schematic illustration of the electrical-component add-on of FIGS. 20A-C in a delivery configuration, in accordance with an application of the present invention.

Reference is still further made to FIG. 21, which is a schematic illustration of electrical-component add-on 430 in a delivery configuration, in accordance with an application of the present invention. For clarity of illustration, a delivery sheath is not shown, even though electrical-component add-on 430 is typically disposed within a delivery sheath when in the delivery configuration, such as described hereinbelow with reference to FIG. 23A.

In some applications of the present invention, electrical-component add-on 430 comprises:

a support 432; and one or more electrical components 40, which are supported by support 432.

Support 432 is configured to assume a delivery configuration, such as shown in FIG. 21, and a deployed configuration, such as shown in FIGS. 18, 19, and 20A-C. Support 432 is configured to be positioned above, at, or below an annulus of a native cardiac valve of a heart, such as described hereinbelow with reference to FIGS. 23B. Support 432 is shaped as a ring 434 when in the deployed configuration, such as shown in FIGS. 18 and 20A-C, so as to receive tubular frame 22 of the prosthetic cardiac valve within support 432, such as shown in FIG. 19.

For some applications, support 432 comprises a wire 460 having a shape memory that causes wire 460 to assume a ring shape when support 432 is in the deployed configuration, such as shown in FIGS. 18, 19, and 20A-C. For some of these applications, wire 460, when having the ring shape, defines more than one turn and fewer than five turns when support 432 is in the deployed configuration.

Optionally, wire 460 is radiopaque and/or support 432 comprises one or more radiopaque markers attached to the support.

For some applications, support 432 comprises an electrical-component mount 462 that assumes an arcuate shape when support 432 is in the deployed configuration, the arcuate shape having an arc length of less than 360 degrees, and, optionally, at least 180 degrees. The one or more electrodes 44 are fixed to electrical-component mount 462.

For some of these applications, wire 460 comprises a metal and electrical-component mount 462 comprises a polymer.

For some of these applications, the one or more electrical components 40 further comprise circuitry 46 and one or more electrical leads 48 that electrically couple the one or more electrodes 44 to circuitry 46 (labeled in FIG. 20B). The one or more electrical leads 48 are integral with electrical-component mount 462. Optionally, electrical-component mount 462 comprises an elongate PCB.

Reference is made to FIGS. 14-21. For some applications, after sterilization during manufacture, electrical-component add-on 330, 340 is inserted into a sterile package. Thus, electrical-component add-on 330, 340 is sterile and is contained within the sterile package. The sterile package does not also contain the prosthetic cardiac valve 20. Optionally, prosthetic cardiac valve 20 is sterile and is contained within a second sterile package, distinct from the sterile package in which electrical-component add-on 330, 340 is contained.

Reference is now made to FIGS. 22A-E, which are schematic illustrations of a delivery system 318 and a method of using delivery system 318 to deploy prosthetic cardiac valve system 310, in accordance with respective applications of the present invention.

Reference is further made to FIGS. 23A-E, which are schematic illustrations of a delivery system 418 and a method of using delivery system 418 to deploy prosthetic cardiac valve system 410, in accordance with respective applications of the present invention.

For some applications, delivery system 318, 418 comprises one or more elongate deployment members 500, such as sutures or wires, that are reversibly coupled to support 332, 432 and configured, while reversibly coupled to support 332, 432, to hold support 332, 432 above, at, or below an annulus 502 of native cardiac valve 16, while tubular frame 22 of prosthetic cardiac valve 20 is unconnected to support 332, 432.

For some applications, support 332, 432 is shaped, when in the deployed configuration, so as to receive tubular frame 22 of prosthetic cardiac valve 20 within support 332, 432 while the one or more elongate deployment members 500 are reversibly coupled to support 332, 432, such as shown in FIGS. 22C-D and 23C-D.

Figures 22A, 22B:
FIGS. 22A-E are schematic illustrations of a delivery system and a method of using the delivery system to deploy the prosthetic cardiac valve system of FIGS. 14 and 15, in accordance with respective applications of the present invention.
Figures 23A, 23B:
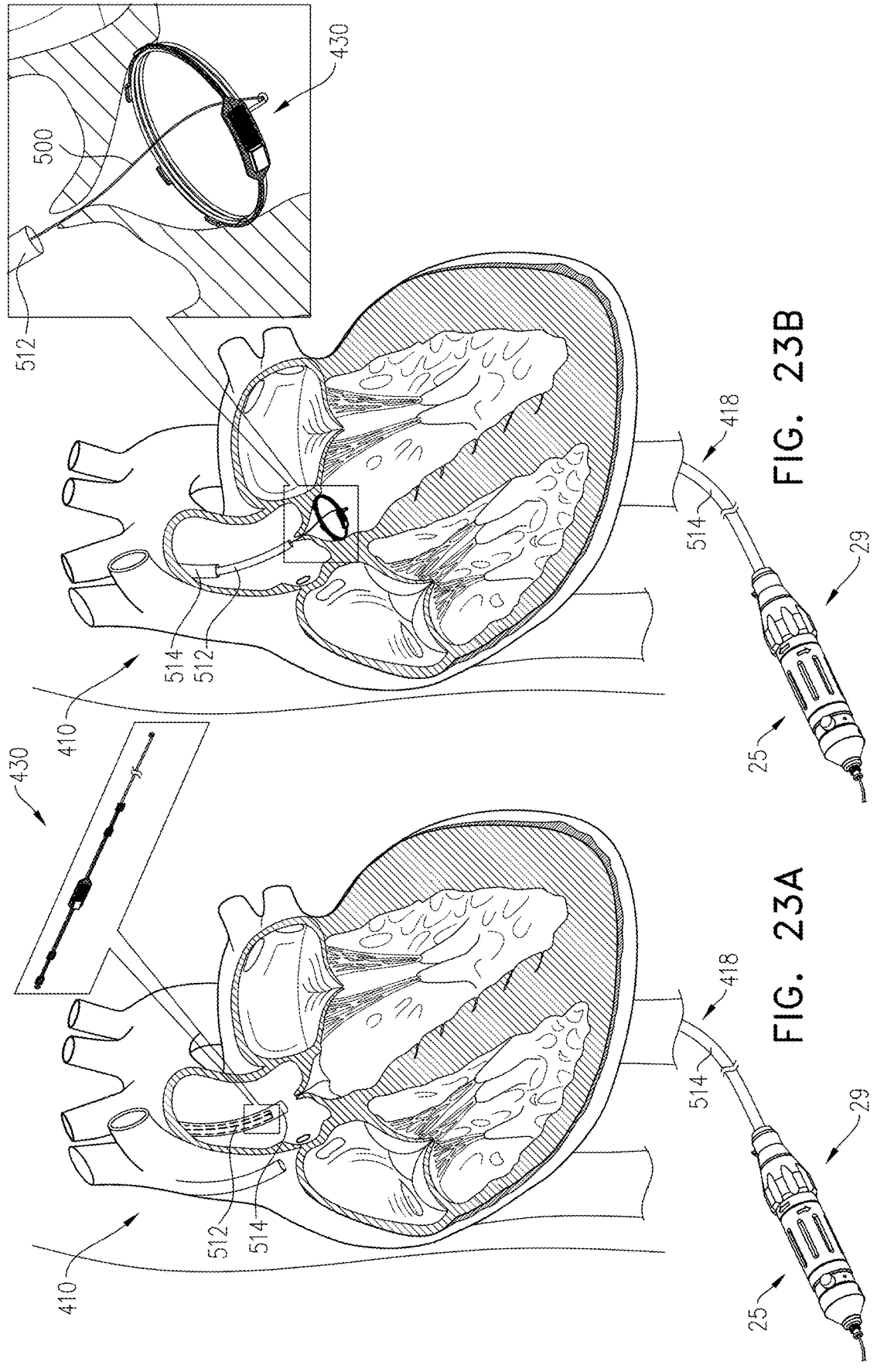
FIGS. 23A-E are schematic illustrations of another delivery system and a method of using the delivery system to deploy the prosthetic cardiac valve system of FIGS. 18 and 19, in accordance with respective applications of the present invention.

Reference is still made to FIGS. 22A-E and 23A-E. In some applications of the present invention, a method is provided that comprises:

advancing support 332, 432 of electrical-component add-on 330, 430 to native cardiac valve 16 while support 332, 432 is in a delivery configuration, such as shown in FIGS. 22A and 23A;

positioning support 332, 432 above (not shown), at (not shown), or below (as shown) annulus 502 and transitioning support 332, 432 from the delivery configuration to a deployed configuration in which support 332 is shaped as ring 334, 434, such as shown in FIGS. 22B and 23B; and thereafter, introducing prosthetic cardiac valve 20 into a body of the patient and placing tubular frame 22 of prosthetic cardiac valve 20 within support 332, 432, as shown in FIGS. 22C-D and 23C-D.

For some applications, positioning support 332, 432 above, at, or below annulus 502 comprises using the one or more elongate deployment members 500 of delivery system 314, 318 to hold support 332, 432 above, at, or below annulus 502 while the one or more elongate deployment members 500 are reversibly coupled to support 332, 432 and while tubular frame 22 of prosthetic cardiac valve 20 is unconnected to support 332, 432, such as shown in FIGS. 22C-D and 23C-D. Typically, electrical-component add-on 330, 430 is advanced to annulus 502 while the add-on is disposed within a delivery sheath 512, such as shown in FIGS. 22A and 23A. Delivery sheath 512 and/or delivery sheath 12 may be introduced through a catheter 514, such as shown.

Figures 22C, 22D:
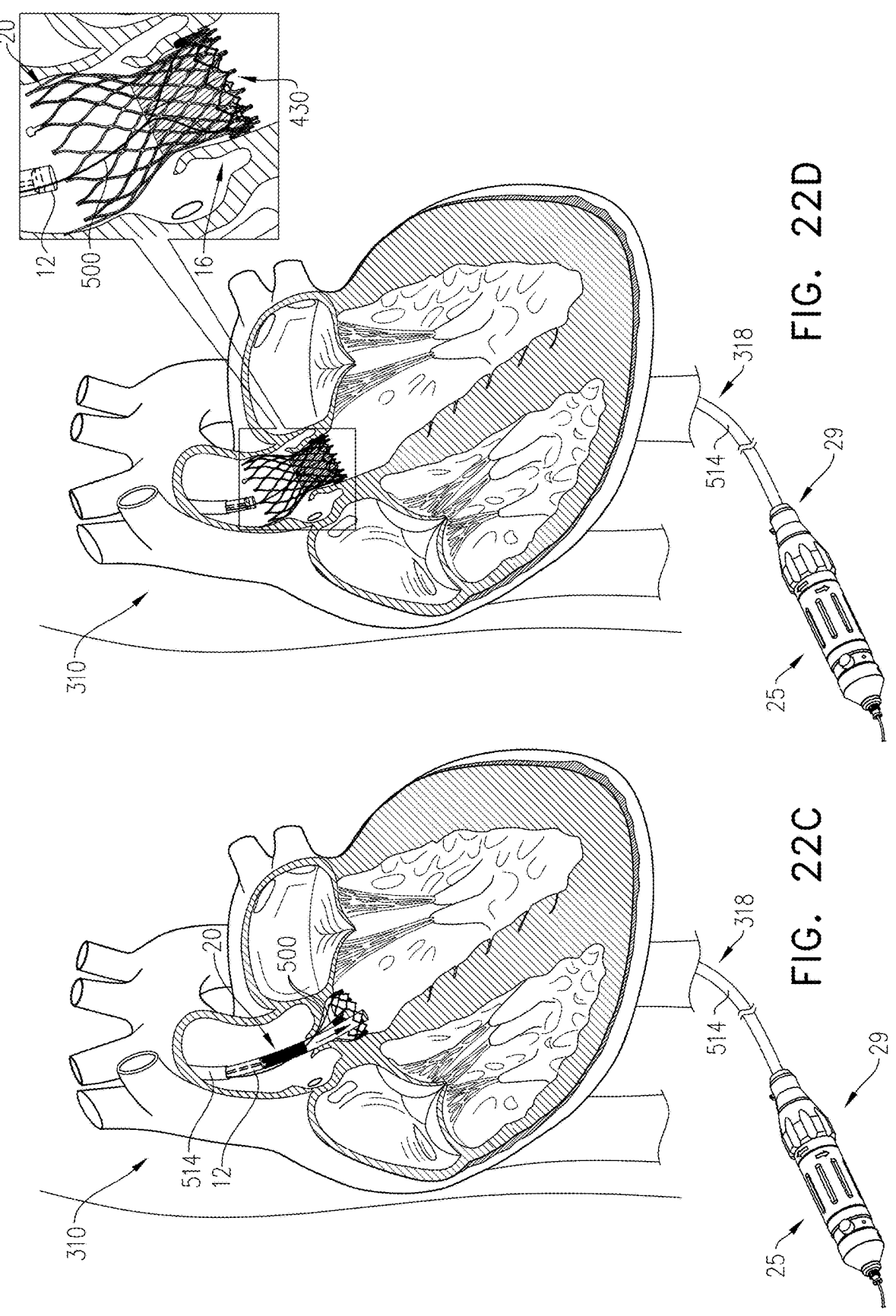
Figure 22E:
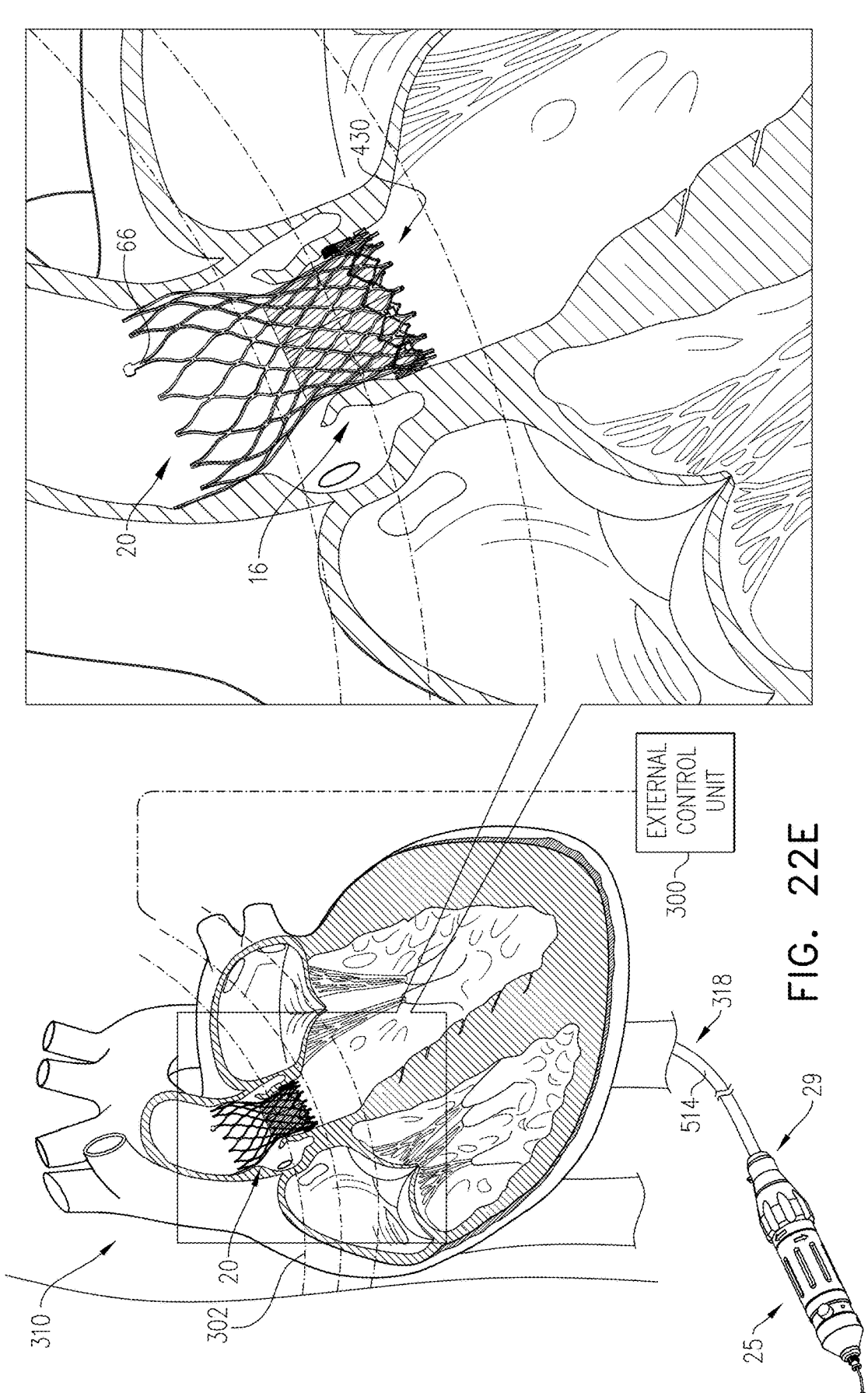
Figures 23C, 23D:
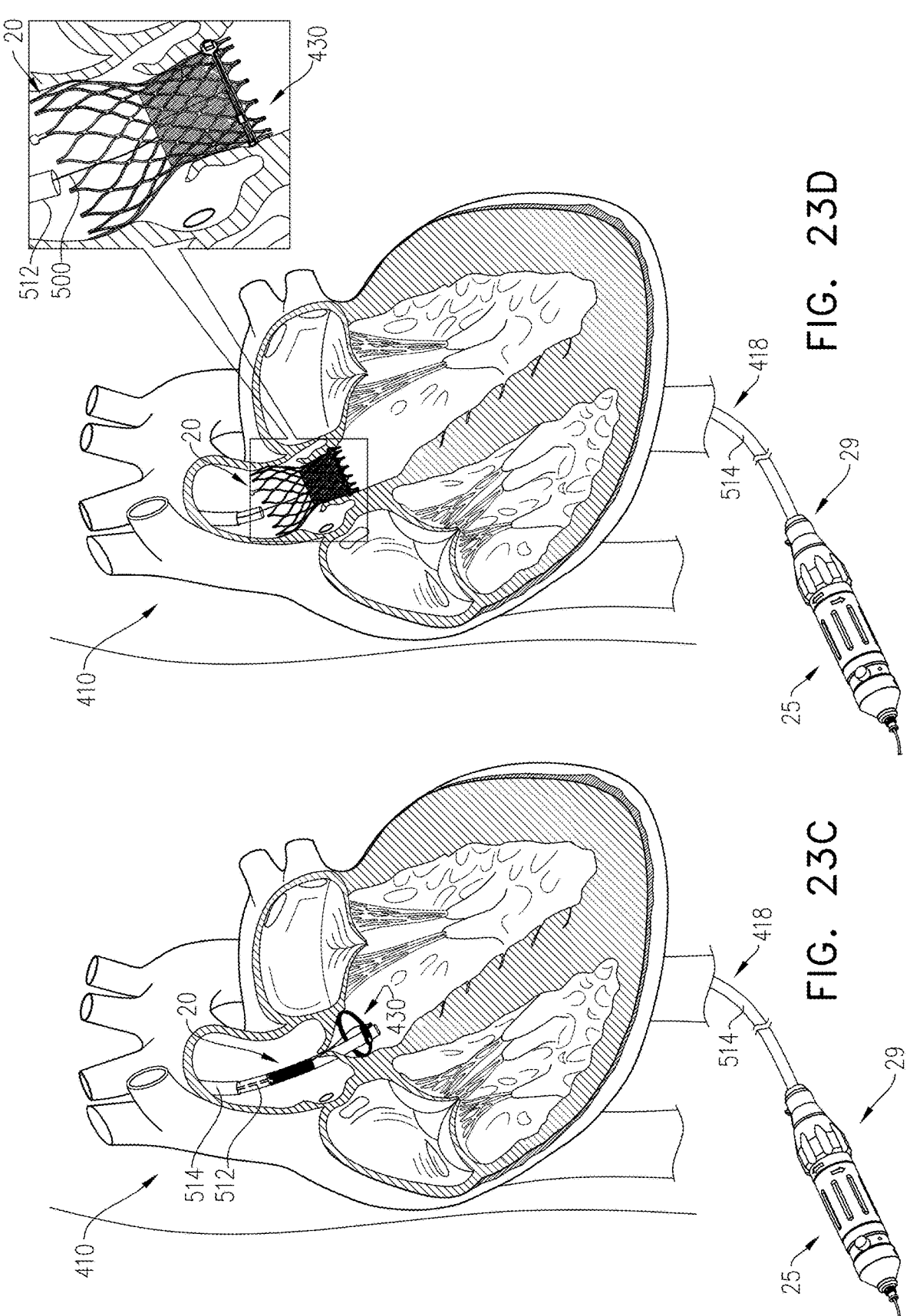
Figure 23E:
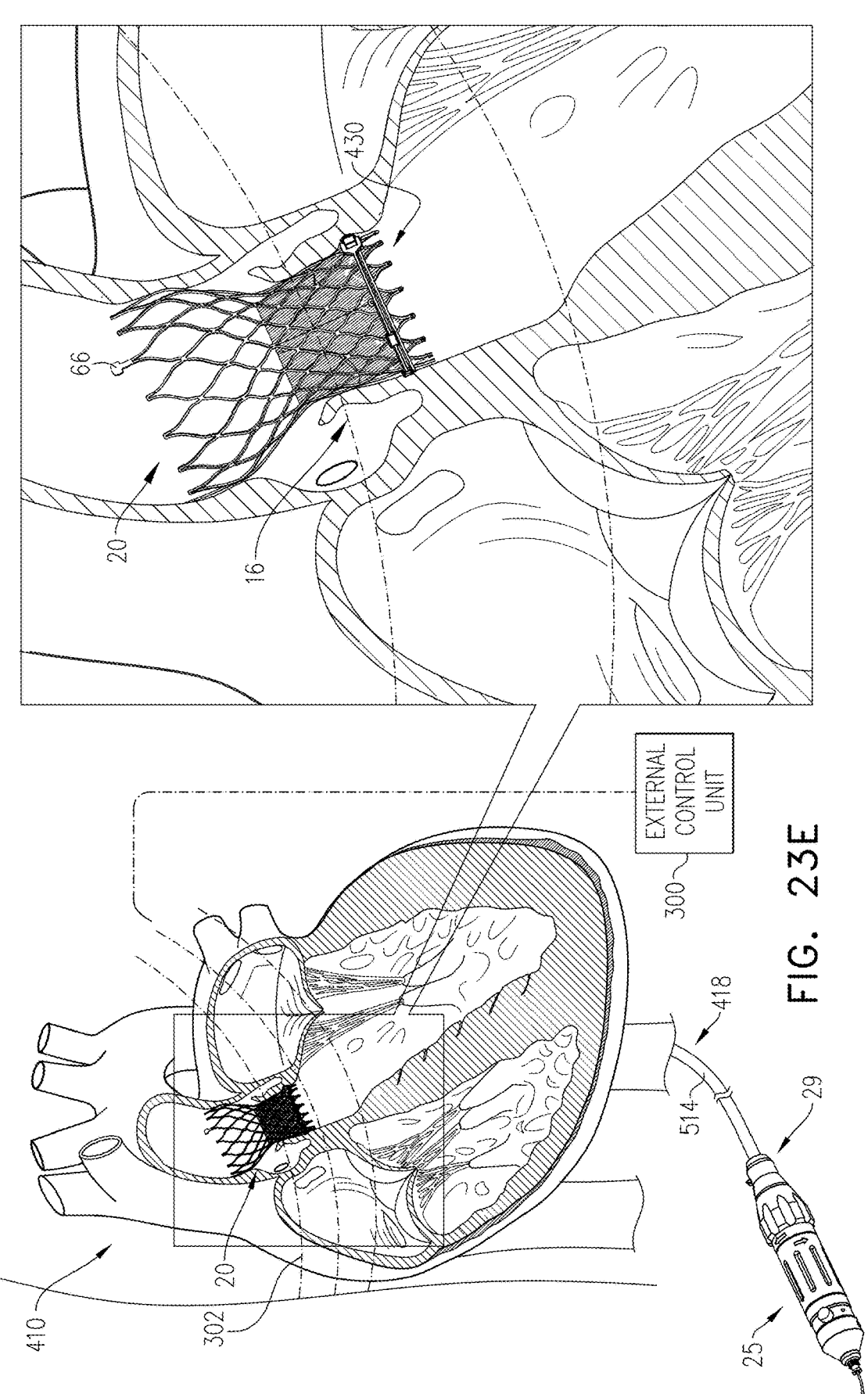

For some of these applications, placing tubular frame 22 within support 332, 432 comprises placing tubular frame 22 within support 332, 432 while the one or more elongate deployment members 500 are reversibly coupled to support 332, 432, such as shown in FIGS. 22C and 23C. The method further comprises decoupling the one or more elongate deployment members 500 from support 332, 432 after placing tubular frame 22 within support 332, 432.

Typically, placing tubular frame 22 of prosthetic cardiac valve 20 within support 332, 432 comprises advancing prosthetic cardiac valve 20 to native cardiac valve 16 while prosthetic cardiac valve 20 is in a constrained delivery configuration within delivery sheath 12, such as described hereinabove with reference to FIG. 13, the techniques of which may be implemented in the present method.

For some applications, such as show in FIG. 22B, placing tubular frame 22 within support 332 comprises radially expanding tubular frame 22 within support 332 to radially expand support 332 and anchor support 332 in place above, at, or below annulus 502.

For some applications, the method further comprises, after positioning support 332, 432 above, at, or below annulus 502, wirelessly transmitting energy to antenna 42, and, for some applications, activating circuitry 46 to pace to the heart using at least one of the one or more electrodes 44.

In an embodiment, techniques and apparatus described in one or more of the following patents and/or applications, which are assigned to the assignee of the present application and are incorporated herein by reference, are combined with techniques and apparatus described herein:

U.S. Pat. No. 10,543,083 to Gross
European Patent Application Publication EP 3508113 A1 to Gross
U.S. Pat. No. 10,835,750 to Gross
U.S. Pat. No. 11,013,597 to Gross
PCT Publication WO 2021/140507 to Gross
PCT Publication WO 2021/224904 to Gross
U.S. Pat. No. 11,065,451 to Gross
U.S. Pat. No. 11,291,844 to Gross
PCT Publication WO 2022/149130 to Gross
U.S. Pat. No. 11,931,255 to Gross et al.
U.S. Pat. No. 11,975,203 to Gross et al.
U.S. patent application Ser. No. 18/607,638, filed Mar. 18, 2024, which published as US Patent Application Publication 2025/0058124 to Gross et al.
International Appl. No. PCT/IL2024/050830, filed Aug. 18, 2024, which published as PCT Publication WO 2025/041129 to Gross et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
advancing a support of an electrical-component add-on to a native cardiac valve of a heart of a patient while the support is in a delivery configuration and the electrical-component add-on is disposed within a delivery sheath, the electrical-component add-on further including one or more electrical components, which are supported by the support, and which include an antenna and one or more electrodes, wherein the support includes a tubular stent that (a) comprises interconnected stent struts and (b) is self-expandable and not balloon-expandable;
positioning the support above, at, or below an annulus of the native cardiac valve and transitioning the support from the delivery configuration to a deployed configuration in which the support is shaped as a ring, by releasing the electrical-component add-on from the delivery sheath such that the tubular stent self-expands; and
thereafter, introducing a prosthetic cardiac valve into a body of the patient and placing a tubular frame of the prosthetic cardiac valve within the support, wherein the prosthetic cardiac valve includes a plurality of prosthetic leaflets coupled to the tubular frame so as to allow blood flow in a proximal downstream direction and inhibit blood flow in a distal upstream direction.

2. The method according to claim 1, wherein the one or more electrical components further include circuitry.

3. The method according to claim 2, further comprising, after positioning the support above, at, or below the annulus, wirelessly transmitting energy to the antenna and activating the circuitry to pace to the heart using at least one of the one or more electrodes.

4. The method according to claim 2,
wherein the one or more electrical components further include one or more electrical leads that electrically couple the one or more electrodes to the circuitry, and
wherein the electrical-component add-on further includes one or more elongate PCBs with which the one or more electrical leads are integral.

5. The method according to claim 1, wherein placing the tubular frame within the support comprises radially expanding the tubular frame within the support to radially expand the support and anchor the support in place above, at, or below the annulus.

6. The method according to claim 1, wherein positioning the support comprises positioning the support below the annulus.

7. The method according to claim 1, wherein the antenna includes at least one prosthetic-valve coil that is not coaxial with the support when the support is in the deployed configuration.

8. The method according to claim 1, wherein the electrical-component add-on does not include valve leaflets.

9. The method according to claim 1, wherein the support is shaped so as to surround a lumen when in the deployed configuration, and wherein the lumen is free of the one or more electrical components.

10. The method according to claim 1, wherein a height of the support, when in the deployed configuration, is 5-15 mm.

11. The method according to claim 1, wherein an outer diameter of the support, when in the deployed configuration, is 19-35 mm.

12. The method according to claim 1, wherein the interconnected stent struts are arranged so as to define interconnected stent cells.

13. The method according to claim 12, wherein the interconnected stent struts are arranged so as to define exactly one or exactly two rows of the interconnected stent cells.

14. The method according to claim 1, further comprising, after positioning the support above, at, or below the annulus, wirelessly transmitting energy to the antenna.

15. A method comprising:
advancing a support of an electrical-component add-on to a native cardiac valve of a heart of a patient while the support is in a delivery configuration, the electrical-component add-on further including one or more electrical components, which are supported by the support, and which include an antenna and one or more electrodes;
positioning the support above, at, or below an annulus of the native cardiac valve using one or more elongate deployment members of a delivery system to hold the support above, at, or below the annulus while the one or more elongate deployment members are reversibly coupled to the support, and while a tubular frame of a prosthetic cardiac valve is unconnected to the support, and transitioning the support from the delivery configuration to a deployed configuration in which the support is shaped as a ring;

thereafter, introducing the prosthetic cardiac valve into a body of the patient and placing the tubular frame of the prosthetic cardiac valve within the support while the one or more elongate deployment members are reversibly coupled to the support, wherein the prosthetic cardiac valve includes a plurality of prosthetic leaflets coupled to the tubular frame so as to allow blood flow in a proximal downstream direction and inhibit blood flow in a distal upstream direction; and decoupling the one or more elongate deployment members from the support after placing the tubular frame within the support.

16. The method according to claim 15, wherein the support includes a tubular stent comprising interconnected stent struts.

17. The method according to claim 16, wherein the tubular stent is self-expandable, wherein advancing the support comprises advancing the support to the native cardiac valve while the support is in the delivery configuration and the electrical-component add-on is disposed within a delivery sheath, and wherein transitioning the support from the delivery configuration to the deployed configuration comprises releasing the electrical-component add-on from the delivery sheath such that the tubular stent self-expands.

18. The method according to claim 15, wherein the support includes a wire having a shape memory that causes the wire to assume a ring shape when the support is in the deployed configuration.

19. The method according to claim 18, wherein the support includes an electrical-component mount that assumes an arcuate shape when the support is in the deployed configuration, the arcuate shape having an arc length of less than 360 degrees, and wherein the one or more electrodes are fixed to electrical-component mount.

20. The method according to claim 19, wherein the one or more electrical components further include circuitry and one or more electrical leads that electrically couple the one or more electrodes to the circuitry, and wherein the one or more electrical leads are integral with electrical-component mount.

21. The method according to claim 18, wherein the wire, when having the ring shape, defines more than one turn and fewer than five turns when the support is in the deployed configuration.

22. The method according to claim 15, wherein placing the tubular frame within the support comprises placing the tubular frame within the support while the one or more elongate deployment members are reversibly coupled to the support, and wherein the method further comprises decoupling the one or more elongate deployment members from the support after placing the tubular frame within the support.

23. The method according to claim 15, wherein the one or more electrical components further include circuitry.

24. The method according to claim 23, further comprising, after positioning the support above, at, or below the annulus, wirelessly transmitting energy to the antenna and activating the circuitry to pace to the heart using at least one of the one or more electrodes.

* * * * *